(12) United States Patent
Armbrust et al.

(10) Patent No.: US 11,141,105 B2
(45) Date of Patent: Oct. 12, 2021

(54) LONG-TERM THERAPEUTIC PRESSURE APPLICATOR AND REAL-TIME MONITORING SYSTEM

(71) Applicant: Somna Therapeutics, LLC, Germantown, WI (US)

(72) Inventors: Daniel Paul Armbrust, Mequon, WI (US); Robert James Grabon, Cedarburg, WI (US); Nick T. Maris, Germantown, WI (US); James S. Miller, Germantown, WI (US); Laura Jackson, Germantown, WI (US); Peter Alex, Cedarburg, WI (US)

(73) Assignee: RESPIRATORY TECHNOLOGY CORPORATION, Houston, TX (US)

( * ) Notice: Subject to any disclaimer, the term of this patent is extended or adjusted under 35 U.S.C. 154(b) by 350 days.

(21) Appl. No.: 15/457,856

(22) Filed: Mar. 13, 2017

(65) Prior Publication Data

US 2017/0258662 A1    Sep. 14, 2017

Related U.S. Application Data

(60) Provisional application No. 62/389,859, filed on Mar. 11, 2016, provisional application No. 62/493,154, filed on Jun. 24, 2016.

(51) Int. Cl.
*A61B 5/00* (2006.01)
*A61C 7/06* (2006.01)
(Continued)

(52) U.S. Cl.
CPC .......... *A61B 5/4848* (2013.01); *A61B 5/6843* (2013.01); *A61C 7/065* (2013.01);
(Continued)

(58) Field of Classification Search
CPC .. A61H 7/00; A61H 7/001; A61H 2201/0184; A61H 2201/0192;
(Continued)

(56) References Cited

U.S. PATENT DOCUMENTS 4,182,344 A    1/1980    Benson
4,230,101 A    10/1980   Gold
(Continued)

FOREIGN PATENT DOCUMENTS

CN    102379733 A    3/2012
WO    03099143 A1    12/2003

OTHER PUBLICATIONS

Almond, et al., A 5-Year Prospective Review of Posterior Partial Fundoplication in the Management of Gastroesophageal Reflux Disease, Int. J. Surg., 2010, 8(3):239-242.
(Continued)

*Primary Examiner* — Justine R Yu
*Assistant Examiner* — Matthew D Ziegler
(74) *Attorney, Agent, or Firm* — Quarles & Brady LLP

(57) ABSTRACT

A therapeutic pressure applicator with a sensor and transceiver is worn by a patient during daily activity to apply pressure to a specific body part, and used in a system with a device such as a cell phone to receive and display real-time pressure data to alert the patient and physician when the pressure is outside a desired range. The applicator includes a securement member and a pressure adjusting device with a pressure adjusting dial, pressure sensing component, pressure focusing plate and cushion. Rotating the dial retracts or extends the sensing component, focusing plate and cushion. The applicator has a computer module with a CPU, memory, transceiver, power source and a force sensor. A pressure button is pressed into engagement with the sensor to transmit real-time focused pressure data to the CPU. The trans- (Continued)

ceiver communicates the real-time cushion pressure data to the cell phone that displays and stores the data.

25 Claims, 22 Drawing Sheets

(51) Int. Cl.
    *A61C 19/04*     (2006.01)
    *A61C 7/14*     (2006.01)
    *A61H 7/00*     (2006.01)
    *A61F 5/01*     (2006.01)
    *A61F 5/32*     (2006.01)

(52) U.S. Cl.
    CPC ............... *A61C 7/14* (2013.01); *A61C 19/04* (2013.01); *A61F 5/01* (2013.01); *A61F 5/32* (2013.01); *A61H 7/001* (2013.01); *A61F 2005/0155* (2013.01); *A61F 2005/0172* (2013.01); *A61F 2005/0188* (2013.01); *A61H 2201/0184* (2013.01); *A61H 2201/0192* (2013.01); *A61H 2201/1207* (2013.01); *A61H 2201/165* (2013.01); *A61H 2201/1695* (2013.01); *A61H 2201/5043* (2013.01); *A61H 2201/5061* (2013.01); *A61H 2201/5097* (2013.01); *A61H 2205/025* (2013.01); *A61H 2205/04* (2013.01)

(58) Field of Classification Search
    CPC ........ A61H 2201/1207; A61H 2201/16; A61H 2201/1602; A61H 2201/1609; A61H 2201/165; A61H 2201/1657; A61H 2201/1664; A61H 2201/1671; A61H 2201/1695; A61H 2201/50; A61H 2201/5007; A61H 2201/501; A61H 2201/5043; A61H 2201/5061; A61H 2201/5097; A61H 2201/0157; A61H 2201/1611; A61H 2201/5071; A61H 2205/025; A61H 2205/04; A61B 5/4848; A61B 5/6843; A61F 5/01; A61F 5/02–028; A61F 5/32; A61F 2005/0155; A61F 2005/0172; A61F 2005/0188
    See application file for complete search history.

(56) References Cited

U.S. PATENT DOCUMENTS

| | | |
|---|---|---|
| 4,243,028 A | 1/1981 | Puyana |
| 4,354,503 A | 10/1982 | Golden |
| 4,366,815 A | 1/1983 | Broomes |
| 4,458,690 A | 7/1984 | O'Connor |
| 4,479,494 A | 10/1984 | McEwen |
| 4,553,934 A | 11/1985 | Armstrong |
| 4,605,010 A * | 8/1986 | McEwen ............ A61B 5/02233 600/499 |
| 4,770,175 A | 9/1988 | McEwen |
| 4,886,070 A | 12/1989 | Demarest |
| 4,924,862 A | 5/1990 | Levinson |
| 4,996,720 A | 3/1991 | Fair |
| 5,024,240 A | 6/1991 | McConnel |
| 5,054,494 A | 10/1991 | Lazzara |
| 5,091,992 A | 3/1992 | Pusic |
| 5,123,425 A | 6/1992 | Shannon, Jr. et al. |
| 5,181,522 A * | 1/1993 | McEwen ............ A61B 5/03 600/561 |
| 5,280,790 A | 1/1994 | Brooks |
| 5,366,438 A | 11/1994 | Martin, Sr. |
| 5,403,266 A | 4/1995 | Bragg et al. |
| 5,483,974 A * | 1/1996 | Crangle ............ A61B 5/03 600/587 |
| 5,487,383 A | 1/1996 | Levinson |
| 5,785,670 A | 7/1998 | Hiebert |
| 5,840,051 A | 11/1998 | Towsley |
| 5,904,662 A | 5/1999 | Myoga |
| 6,056,711 A | 5/2000 | Domanski et al. |
| 6,200,285 B1 | 3/2001 | Towliat |
| 6,422,873 B1 | 7/2002 | Abdelatti |
| 6,890,285 B2 | 5/2005 | Rahman |
| 7,052,465 B1 | 5/2006 | Lunak |
| 7,909,786 B2 * | 3/2011 | Bonnefin ............ A61H 9/0078 601/151 |
| 8,382,665 B1 | 2/2013 | Fam |
| 8,640,710 B2 | 2/2014 | Matthews |
| D724,225 S | 3/2015 | Maris |
| 9,289,136 B2 | 3/2016 | Addison |
| 9,468,552 B2 | 10/2016 | Thibeault |
| 9,526,449 B2 | 12/2016 | Shaker |
| 2001/0011543 A1 | 8/2001 | Forsell |
| 2003/0070684 A1 | 4/2003 | Saied |
| 2003/0135120 A1 | 7/2003 | Parks et al. |
| 2003/0229375 A1 | 12/2003 | Fleischer |
| 2004/0097816 A1 | 5/2004 | Just et al. |
| 2004/0138586 A1 | 7/2004 | Ganz et al. |
| 2005/0059909 A1 * | 3/2005 | Burgess ............ A61F 7/007 601/15 |
| 2005/0085753 A1 | 4/2005 | Ducharme et al. |
| 2005/0228302 A1 | 10/2005 | Dalgaard et al. |
| 2006/0004304 A1 | 1/2006 | Parks |
| 2006/0074362 A1 * | 4/2006 | Rousso ............ A61H 11/02 601/152 |
| 2006/0194179 A1 | 8/2006 | Abdelatti |
| 2007/0038132 A1 | 2/2007 | Kishimoto et al. |
| 2007/0106166 A1 | 5/2007 | Somberg |
| 2007/0219588 A1 | 9/2007 | Freeman |
| 2007/0239092 A1 * | 10/2007 | Ross ............ A61F 5/28 602/20 |
| 2008/0086179 A1 | 4/2008 | Sharma |
| 2008/0161730 A1 | 7/2008 | McMahon et al. |
| 2008/0167675 A1 | 7/2008 | Hogosta et al. |
| 2008/0262479 A1 * | 10/2008 | Barela ............ A61B 5/01 606/1 |
| 2009/0003669 A1 | 1/2009 | Parks et al. |
| 2009/0044799 A1 | 2/2009 | Qiu |
| 2009/0300831 A1 | 12/2009 | Welch |
| 2010/0022987 A1 | 1/2010 | Bochenko et al. |
| 2011/0112448 A1 * | 5/2011 | Wu ............ A42B 3/145 601/85 |
| 2011/0202089 A1 * | 8/2011 | Sun ............ A61B 17/1325 606/201 |
| 2012/0150215 A1 * | 6/2012 | Donald ............ A61B 17/1325 606/203 |
| 2012/0190938 A1 | 7/2012 | Addington et al. |
| 2012/0203132 A1 * | 8/2012 | Blumensohn ......... A61H 11/00 600/546 |
| 2013/0090573 A1 | 4/2013 | Shaker |
| 2013/0102930 A1 | 4/2013 | Connor |
| 2013/0184621 A1 * | 7/2013 | Ma ............ A61H 7/004 601/134 |
| 2013/0304112 A1 * | 11/2013 | Ting ............ A61B 5/021 606/203 |
| 2014/0257156 A1 | 9/2014 | Capra |
| 2015/0112380 A1 * | 4/2015 | Heller ............ A61H 7/001 606/201 |
| 2015/0119773 A1 * | 4/2015 | Flannery ............ A61B 17/1325 601/152 |
| 2015/0335284 A1 * | 11/2015 | Nuovo ............ A61B 5/0022 600/301 |
| 2016/0095605 A1 | 4/2016 | Maris |
| 2016/0375265 A1 * | 12/2016 | Kim ............ A61H 39/04 607/89 |

OTHER PUBLICATIONS

Aslam, et al., Performance and Optimal Technique for Pharyngeal Impedance Recording: A Simulated Pharyngeal Reflux Study, American Journal of Gastroenterology, 2007, 102:33-39.

Chang, et al., Systematic Review and Meta-Analysis of Randomised Controlled Trials of Gastro-Oesophageal Reflux Interventions for

(56) References Cited

OTHER PUBLICATIONS

Chronic Cough Associated with Gastro-Oesophageal Reflux, BMJ, doi:10.1136/bmj.38677.559005.55, Published Dec. 5, 2005, 7 pages.
Chen, et al., Sleep Symptoms and Gastroesophageal Reflux, J. Clin. Gastroenterol., 2008, 42:13-17.
DeLegge, Aspiration Pneumonia: Incidence, Mortality, and At-Risk Populations, Journal of Parenteral and Enteral Nutrition, 2002, 26(6):S19-S25.
Dickman, et al., Relationships Between Sleep Quality and pH Monitoring Findings in Persons with Gastroesophageal Reflux Disease, Journal of Clinical Sleep Medicine, 2007, 3(5):505-513.
Dimarino, Jr., et al., The Effect of Gastro-Oesophageal Reflux and Omeprazole on Key Sleep Parameters, Alimentary Pharmacology & Therapeutics, 2005, 22:325-329.
Eisenstadt, Dysphagia and Aspiration Pneumonia in Older Adults, Journal of the American Academy of Nurse Practitioners, 2010, 22:17-22.
Ewart, The Efficacy of Cricoid Pressure in Preventing Gastro-Oesophageal Reflux in Rapid Sequence Induction of Anaesthesia, J. Perioper. Pract., 2007, 17(9):432-436.
Farup, et al., The Impact of Nocturnal Symptoms Associated with Gastroesophageal Reflux Disease on Health-Related Quality of Life, Arch. Intern. Med., 2001, 161:45-52.
Fass, et al., Predictors of Heartburn During Sleep in a Large Prospective Cohort Study, Chest, 2005, 127:1658-1666.
Freid, The Rapid Sequence Induction Revisited: Obesity and Sleep Apnea Syndrome, Anesthesiology Clinics of North America, 2005, 23:551-564.
Furnee, et al., Symptomatic and Objective Results of Laparoscopic Nissen Fundoplication After Failed EndoCinch Gastroplication for Gastro-Oesophageal Reflux Disease, European Journal of Gastroenterology & Hepatology, 2010, 22(9)1118-1122.
Gatta, et al., Meta-Analysis: The Efficacy of Proton Pump Inhibitors for Laryngeal Symptoms Attributed to Gastro-Oesophageal Reflux Disease, Alimentary Pharmacology & Therapeutics, 2007, 25:385-392.
Gerson, et al., A Systematic Review of the Definitions, Prevalence, and Response to Treatment of Nocturnal Gastroesophageal Reflux Disease, Clinical Gastroenterology and Hepatology, 2009, 7:372-378.
Hancox, et al., Associations Between Respiratory Symptoms, Lung Function and Gastro-Oesophageal Reflux Symptoms in a Population-Based Birth Cohort, Respiratory Research, 2006, 7:142, 9 pages.
Hunter, et al., A Physiologic Approach to Laparoscopic Fundoplication for Gastroesophageal Reflux Disease, Annals of Surgery, 1996, 223(6):673-687.
King, et al., Trachael Tube Cuffs and Tracheal Dilatation, Chest, 1975, 67:458-462.
Kubota, et al., Tracheal Compression to Prevent Aspiration and Gastric Distension, Can J Anaesth, 1992, 39:2, p. 202.
Kumar, et al., Persistent Pneumonia: Underlying Cause and Outcome, Indian Journal of Pediatrics, 2009, 76(12):1223-1226.
Landsman, Cricoid Pressure: Indications and Complications, Pediatric Anesthesia, 2004, 14(1):43-47.
Lawes, et al., The Cricoid Yoke—A Device for Providing Consistent and Reproducible Cricoid Pressure, British Journal of Anaesthesia, 1986, 58(8):925-931.
Locke, et al., Prevalence and Clinical Spectrum of Gastroesophageal Reflux: A Population-Based Study in Olmsted County, Minnesota, Gastroenterology, 1997, 112:1448-1456.
McGuigan, et al., Review Article: Diagnosis and Management of Night-Time Reflux, Alimentary Pharmacology & Therapeutics, 2004, 20(Suppl. 9):57-72.
Mylotte, et al., Pneumonia Versus Aspiration Pneumonitis in Nursing Home Residents: Prospective Application of a Clinical Algorithm, J. Am. Geriatr. Soc., 2005, 53:755-761.
Neilipovitz, et al., No Evidence for Decreased Incidence of Aspiration After Rapid Sequence Induction, Can. J. Anesth., 2007, 54:9, pp. 748-764.
Orr, Review Article: Sleep-Related Gastro-Oesophageal Reflux as a Distinct Clinical Entity, Alimentary Pharmacology & Therapeutics, 2010, 31:47-56.
Palombini, et al., A Pathogenic Triad in Chronic Cough—Asthma, Postnasal Drip Syndrome, and Gastroesophageal Reflux Disease, Chest, 1999, 116:279-284.
Parry, Teaching Anaesthetic Nurses Optimal Force for Effective Cricoid Pressure: A Literature Review, Nursing in Critical Care, 2009, 14(3):139-144.
Pfitzner, et al., Controlled Neck Compression in Neurosurgery, Anaesthesia, 1985, 40(7):624-629.
Priebe, Cricoid Pressure: An Expert's Opinion, Minerva Anestesiologica, 2009, 75(12):710-714.
Rakita, et al., Laparoscopic Nissen Fundoplication Offers High Patient Satisfaction with Relief of Extraesophageal Symptoms of Gastroesophageal Reflux Disease, The American Surgeon, 2006, 72:207-212.
Roka, et al., Prevalence of Respiratory Symptoms and Diseases Associated with Gastroesophageal Reflux Disease, Digestion, 2005, 71:92-96.
Sale, Prevention of Air Embolism During Sitting Neurosurgery, Anaesthesia, 1984, 39(8):795-799.
Shaker, et al., Nighttime Heartburn Is an Under-Appreciated Clinical Problem That Impacts Sleep and Daytime Function: The Results of a Gallup Survey Conducted on Behalf of the American Gastroenterological Association, The American Journal of Gastroenterology, 2003, 98(7):1487-1493.
Shaker, et al., Intrapharyngeal Distribution of Gastric Acid Refluxate, The Laryngoscope, 2003, 113:1182-1191.
Shaker, Nighttime GERD: Clinical Implications and Therapeutic Challenges, Best Practice & Research Clinical Gastroenterology, 2004, 18(S):31-38.
So, et al., Outcomes of Atypical Symptoms Attributed to Gastroesophageal Reflux Treated by Laparoscopic Fundoplication, Surgery, 1998, 124:28-32.
Stroud, et al., Management of Intractable Aspiration, Oct. 18, 2000, 10 pages.
Suiter, et al., Effects of Cuff Deflation and One-Way Tracheostomy Speaking Valve Placement on Swallow Physiology, Dysphagia, 2003, 18:284-292.
Ulualp, et al., Pharyngo-UES Contractile Reflex in Patients with Posterior Laryngitis, The Laryngoscope, 1998, 108(9):1354-1357.
Vanner, et al., Upper Oesophageal Sphincter Pressure and the Effect of Cricoid Pressure, Anaesthesia, 1992, 47:95-100.
Wileman, et al., Medical Versus Surgical Management for Gastro-Oesophageal Reflux Disease (GORD) in Adults (Review), The Cochrane Library, 2010, Issue 4, 39 pages.
Young, et al., Evaluation of a New Design of Tracheal Tube Cuff to Prevent Leakage of Fluid to the Lungs, British Journal of Anaesthesia, 1998, 80:796-799.

* cited by examiner

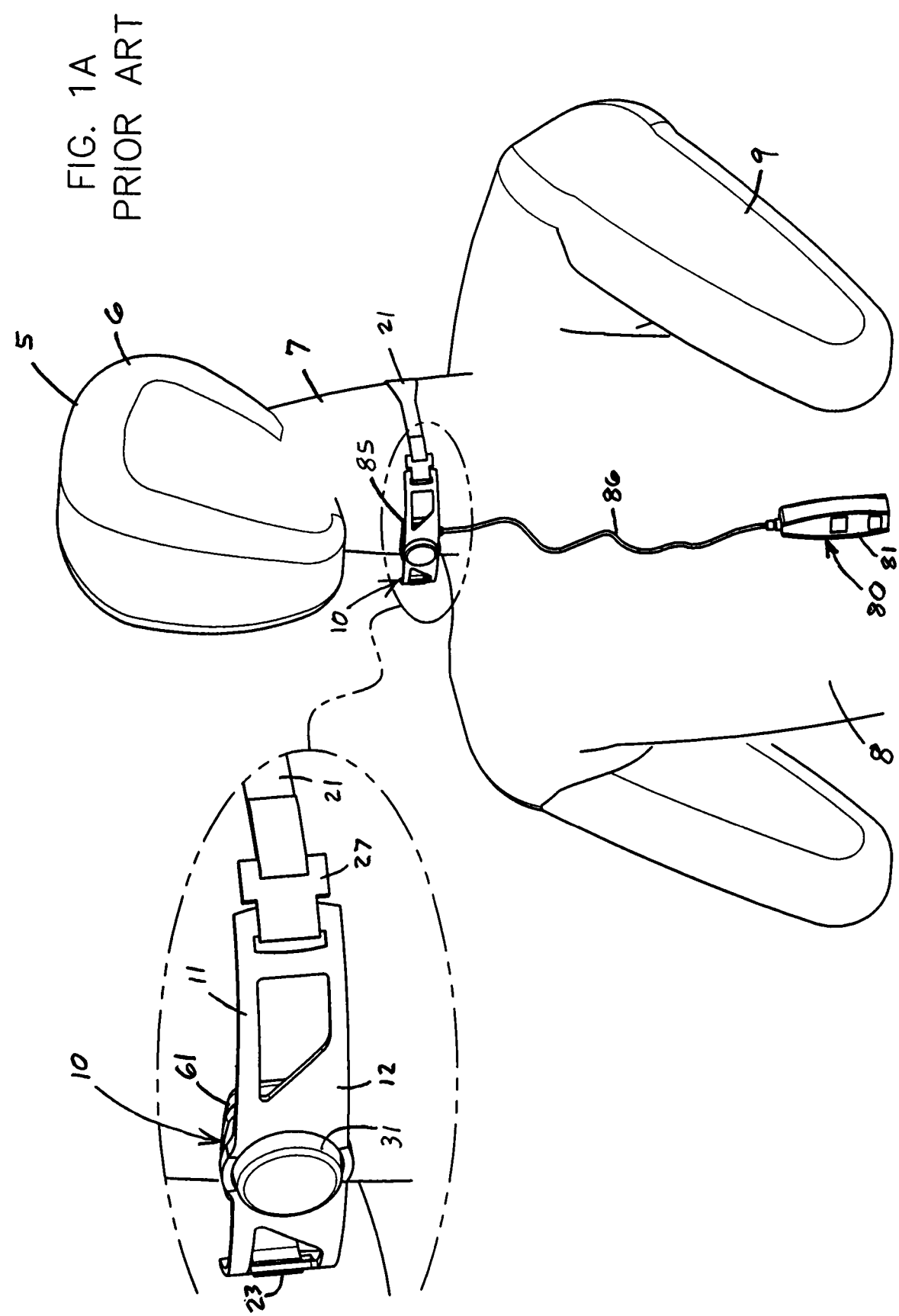

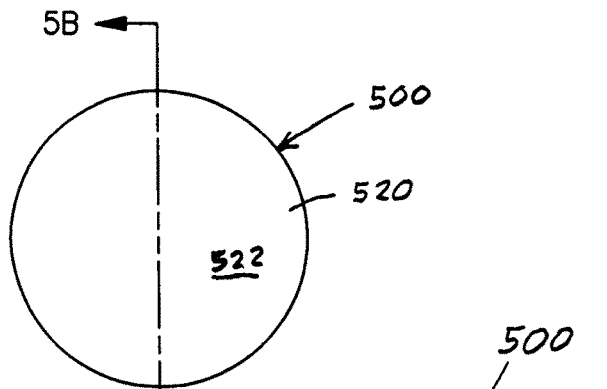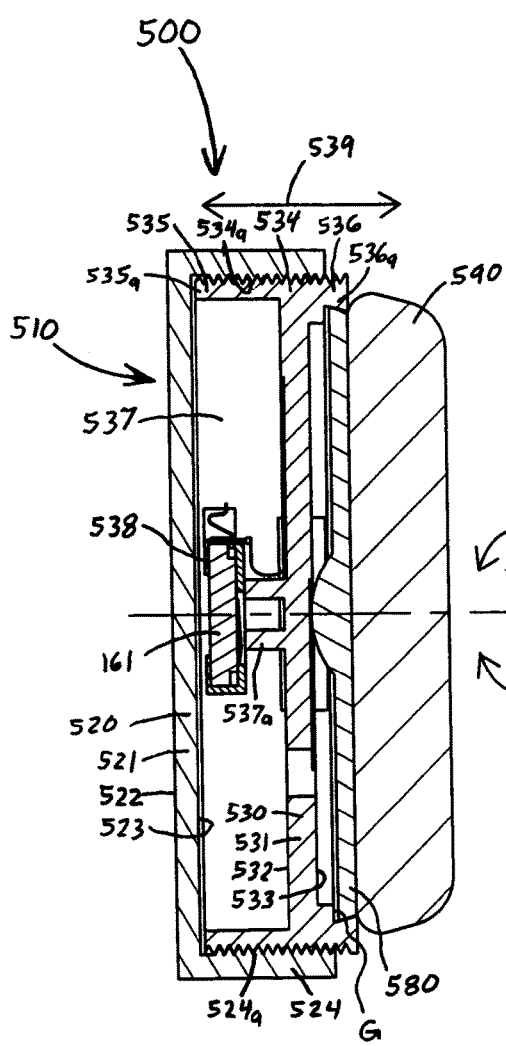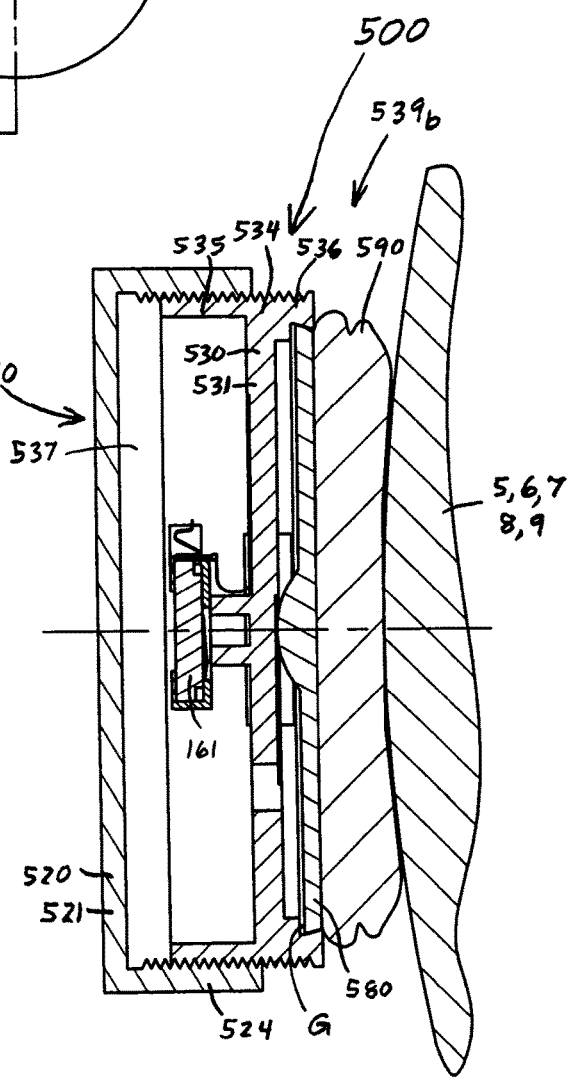
FIG. 5A
FIG. 5B
FIG. 5C

LONG-TERM THERAPEUTIC PRESSURE APPLICATOR AND REAL-TIME MONITORING SYSTEM

TECHNICAL FIELD OF THE INVENTION

This invention relates to a therapeutic pressure applicator worn by a patient during normal daily activity to apply pressure to a specific body part and obtain real-time pressure data during long-term medical treatment, and used in a system including a device such as a cell phone to receive and display the pressure data to alert the patient and treating physician when the pressure is outside a desired range.

BACKGROUND OF THE INVENTION

Medical devices to apply compression or tension to the head 6, neck 7, torso 8, arm 9 or other body part of a patient (see FIG. 1A) are well known. Conventional blood pressure monitors are secured to the arm, and inflate and deflate to determine blood pressure. Examples of these monitors are disclosed in U.S. Pat. No. 4,458,690 to O'Connor, U.S. Pat. No. 5,054,494 to Lazzara, U.S. Pat. No. 5,280,790 to Brooks, U.S. Pat. No. 7,052,465 to Lunak and U.S. Pat. No. 9,289,136 to Addison. Back braces are secured to the torso to apply pressure to specific portions of the spine to treat disorders involving the curvature of the spine such as scoliosis. Examples of back braces are disclosed in U.S. Pat. No. 4,230,101 to Gold, U.S. Pat. No. 5,840,051 to Towsley and U.S. Pat. No. 9,468,552 to Thibeault. Orthodontic headgear treats bite disorders and properly align teeth by applying force to the teeth. Examples of headgear are disclosed in U.S. Pat. No. 4,555,934 to Armstrong and U.S. Pat. No. 8,640,710 to Matthews. The REZA BAND® device applies pressure to the esophagus of a patient suffering from reflux disorders, and is disclosed in U.S. patent application Ser. No. 13/702,258 to Reza Shaker, the disclosure of which is incorporated by reference. While some devices such as blood pressure monitors or traction in a hospital bed require patients to remain immobile, other devices such as back braces, orthodontic headgear and the REZA BAND® device allow mobility so patients live relatively normal ambulatory lives during treatment. These ambulatory devices are secured to the patient by their treating physician. The physician ensures the device is properly applied to the patient and sets the device to apply a desired amount of force or pressure. The patient then wears the device at home and during daily activities, and returns to the physician at scheduled weekly or monthly intervals until the treatment is completed.

The REZA BAND® device 10 is secured to the neck 7 of a person 5 to apply pressure to his or her upper esophageal sphincter as shown in FIGS. 1A-D. The REZA BAND® device 10 includes a neck band 11 with a curved, semi-flexible strap bracket 12. The strap bracket 12 has a central recess 13, front and rear surfaces 14 and 15, a central opening 17 and opposed lateral ends 18. The rear surface 15 of the strap bracket 12 has two spaced slots 15a. The common center of the central recess 13 and opening 17 forms a centerline 19 for the device 10. A flexible strap 21 is secured to each lateral end 18 to fit the device 10 to the neck 7 of a patient 5. One end 22 of the strap 21 is secured by a selectively adjustable Velcro® fastener 23, and its other end 26 is secured by a non-adjustable rigid clip fastener 27.

The REZA BAND® device 10 includes a compression mechanism 30 with a pressure dial 31, a pressure plate 51 and a cushion 61. The dial 31 has a knob 32 formed by an outer shell 34 with a generally hemispherical shape that forms an interior chamber 35. The rear end of the knob 32 forms a rim 37 with inwardly extending tabs. The dial 31 also has a circular base 42 that is flushly and rotatably received by the circular recess 13 of the strap bracket 12. The circular base 42 has a flat rear surface 43 and a central opening 45 with a threaded sidewall 46. The rear surface of the base 42 rotatingly engages the flat surface of the bracket recess 13. The rim of the knob 32 is firmly joined to a rim 47 of the base 42. The rim 47 has tabs that mate with the knob tabs so that the knob 32 and base 42 rotate in unison.

The pressure plate 51 has front and rear surfaces 52 and 53, and a thickness of about 0.125 inches. The plate 51 has a generally rectangular shape with a width of about 1.125 inches and length of about 1.625 inches. A thin rectangular shaped Velcro® strip fastener 54 is secured to the rear surface 52. A central post or stem 55 with a threaded sidewall 56 extends from the front surface 53 a distance of about 0.375 inches. The stem has a diameter of about 0.25 inches. The stem 55 extends unobstructedly through the larger diameter, unthreaded bracket opening 17, with its threaded sidewall 56 in mating threaded engagement with the threaded sidewall 46 of the dial base opening 45. Two mounting and anti-rotation posts 57 are located proximal the longitudinal edges of the plate 51 and straddle the central stem 55. The posts 57 extend forward from its front surface 52, and are flushly received by the bracket slots 15a. The posts 57 have shoulders 57a that form a limit stop to limit the retracting movement of the plate 51. A washer 58 is secured by a screw fastener 59 to the front or top surface of the stem 55. The diameter of the washer 58 is larger than the dial base opening 45 to form an additional limit stop to prevent the overextension of the pressure plate 51 into the neck 7 of the patient 5.

The cushion 61 is secured by a Velcro® strip 65 to the rear surface 53 of the pressure plate 51. The cushion 61 is relatively soft and deformable to conform to the shape of the front portion of the neck 7 and throat of the patient 5 and alleviate any uncomfortable pinch points between the pressure plate 51 and the soft tissue of the neck 7. The Velcro® strip fastener 65 allows for the removal of the cushion 61 so it can be periodically washed or replaced during the use of the band 10.

The treating physician secures the REZA BAND® device 10 to the patient 5 in two steps. First, with the clip 27 secured to the bracket 12, the treating physician selectively positions and secures the Velcro® fastener 23 to achieve an approximate pressure close to the desired pressure on the throat or esophagus of the patient 5. Second, the physician uses the pressure dial 31 to set the device 10 to the desired or prescribed pressure. Rotating the pressure dial 31 in one direction increases pressure on the esophagus by causing the threaded central stem 55 and pressure plate 51 to move longitudinally along a path of travel 70 away from the bracket 12 and toward the neck 7 to an increased pressure position 71 as best shown in FIGS. 1C and 1D. The strap bracket 12 flexes slightly. The plate guide posts 57 remain in flush engagement inside bracket slots 15a. Rotating the pressure dial 31 in an opposite direction decreases pressure on the esophagus by causing the threaded central stem 55 and pressure plate 51 to move longitudinally along the path of travel 70 toward the strap bracket 12 and away from the neck 7 and into a decreased pressure position 72.

The treating physician uses a separate pneumatic gauge 80 to determine the pressure of the REZA BAND® device 10 on the throat or neck 7. This gauge 80 includes a pressure gauge 81, an inflatable pad 85 and a connecting tube 86.

After the Velcro® strap fastener 23 is secured and the pressure dial 31 is rotated to obtain and set pressure, the physician removes the pressure pad 75. The pneumatic gauge 80 remains at the office of the physician, and does not go home with the patient. During the use of the band 10, the patient 5 should use the rigid clip 27 to remove and reattach the band when bathing, or for formal occasions, physical activity, etc. By using the clip 27, the patient 5 does not inadvertently alter the prescribed pressure of the device 10.

A problem with conventional medical devices that apply force or pressure to a patient is that they do not display the actual force or pressure being applied. Between periodic physician visits, the pressure can deviate from the desired or prescribed amount. For example, the device can slide or shift up or down on the patient, the patient can lose or gain weight, experience swelling or become dehydrated, which can cause the applied force or pressure to increase or decrease. The patient has no accurate way to tell how much the pressure has deviated from that set desired amount. A patient can only guess based on his or her past recollection of how the device felt several hours, days, weeks or months before. Gradual increases or decreases over time can go unnoticed. Without realizing it, the patient can allow the device to gradually increase or decrease to an improper or even potentially harmful setting. In other situations, the patient will incorrectly believe the force or pressure has changed and is now too loose or tight, when the force or pressure has not changed. The patient will then improperly adjust the device to increase or decrease the force or pressure to an improper or harmful setting.

Another problem with conventional medical devices that apply force or pressure to a patient is that they do not provide any objective evidence to the physician regarding the use of the device by the patient. The physician must rely on the patient to tell him or her that the device was worn, when the device was worn, and if the desired pressure was applied when the device was worn. Should the patient forget these details or fail to accurately describe these details, the physician may not be able to take the proper course of action in treating the patient.

A further problem with conventional medical devices that apply force or pressure is that they do not alert or warn the patient when the pressure has increased or decreased outside a medically desirable range.

A still further problem with conventional medical devices that apply force or pressure to a patient is the imprecision in setting the devices. For example, when the treating physician sets a REZA BAND® device 10 to a desired pressure, the physician uses a pressure gauge 80 with an inflated pneumatic pad 85 placed between the band and the neck 7 of the patient 5 as shown in FIG. 1A. The pressure applied by the band 10 against the esophagus is measured with the pad 85 in place. Once the pressure is set, the physician removes the pad 85, which stays at the office of the physician with the pressure gauge 80. Yet, the inflated pad 85 has a significant thickness. When the pad 85 is removed, the pressure exerted by the band 10 on the esophagus decreases so that the actual pressure applied by the band 10 to the neck 7 is unknown.

A still further problem with conventional medical devices that apply force or pressure to a patient is that they have both a pressure setting fastener and a quick release fastener. In devices such as a REZA BAND® device 10, the pressure setting fastener includes a Velcro® strip 23 that is secured by the physician. The quick release fastener 27 allows the patient to remove the device without altering or adjusting the Velcro® strip fastener 23 set by the physician. The clip 27 allows the patient to temporarily remove the device to do a particular activity such as take a bath, exercise, go swimming or clean the device, and then reattach the device without altering or adjusting the pressure setting of the Velcro® fastener 23. Unfortunately, a patient can forget which fastener is which, and use the Velcro® fastener 23 to take off the device. When reattaching the device, the patient will then use his or her best guess of the prescribed set pressure to reattach the device. This leads to the application of an improper or even harmful pressure setting.

A still further problem of conventional medical devices that apply force or pressure is their bulkiness. Although the devices are intended to allow patients to live relatively normal ambulatory lives, they are large and cumbersome, and extend out from the body so much that they become awkward to wear when doing normal activities.

The present invention is intended to solve these and other problems.

BRIEF DESCRIPTION OF THE INVENTION

This invention pertains to a therapeutic pressure applicator equipped with a sensor and transceiver worn by a patient during normal daily activity to apply pressure to a specific body part during long-term medical or therapeutic treatment, and used in a system with a device such as a cell phone to receive and display real-time pressure data to alert the patient and treating physician when the pressure is outside a desired range. The applicator includes a securement member and a pressure adjusting device with a pressure adjusting dial, pressure control component, pressure focusing plate and cushion. Rotating the dial retracts or extends the control component, focusing plate and cushion. The applicator has a computer module with a CPU, memory, transceiver, power source and a force sensor. The focusing plate aligns a pressure button into pressed engagement with the sensor to transmit real-time focused pressure data, which the CPU converts into real-time cushion pressure data. The transceiver periodically communicates the long-term, real-time cushion pressure data to the cell phone to display and store the data.

An advantage of the present therapeutic pressure applicator and monitoring device and monitoring system is the monitoring system displays the real-time cushion pressure being applied to the patient. When the cushion pressure deviates from the desired amount set by the physician, a device such as a cell phone will display the real-time cushion pressure, and alert the patient that the pressure has deviated or is not within a desired pressure range. The patient does not have to guess the current pressure level based on his or her past recollection of how the device felt. Gradual increases or decreases over time are readily displayed. The display of the real-time cushion pressure level also helps prevent the patient from incorrectly believing the pressure has changed, when in fact it has not changed.

Another advantage of the present therapeutic pressure applicator and monitoring system is that the long-term, real-time cushion pressure data can be readily stored and communicated to the treating physician. The device and system provide the physician with objective evidence regarding if the device was worn, when the device was worn, and if the device was within the desired pressure setting during the time it was worn.

A further advantage of the present therapeutic pressure applicator and monitoring system is that it alerts or warns the patient when the pressure has increased or decreased outside a prescribed pressure range. This warning can be performed visually, audibly, or otherwise. The screen of the cell phone or personal computer is green when the real-time pressure is at a desired level, and turns red when the real-time pressure is outside the desired pressure setting or range. The cell phone or personal computer can also sound an audible alarm to notify the patient of the pressure deviation or potentially harmful situation.

A still further advantage of the therapeutic pressure applicator and monitoring system is that the patient can use his or her cell phone to transmit the data to the physician via the wireless telecommunication to a phone or computer in the office of the physician or use the personal computer of the patient to send days, weeks or months or real-time cushion pressure data via a land line, such as via an email with the attached data. The patient does not need to schedule an appointment or drive to the office of the physician to deliver the data. The physician and patient do not need to remove the applicator to obtain the long-term, real-time cushion pressure data.

A still further advantage of the therapeutic pressure applicator and monitoring system is the adaptability and accuracy of the real-time pressure readings gathered. The device includes a focusing plate that collects the distributed pressure forces across the cushion being pressed into the body of the patient and focuses that force or pressure via a curved button on a small sensor contact zone. This magnifies the sensitivity of the sensor so that even slight variations in the pressure distribution can be observed. The curved button is also free to rock or rotate slightly so that an uneven cushion pressure distribution about the centerline of the device does not change the size of the contact zone, so the observed pressure by the sensor does not improperly read an increase in pressure when none has occurred. The devices adjusts to accommodated anomalies in the body surface such as a scare, cyst or underlying bone or cartilage and still provides accurate cushion pressure readings.

A still further advantage of the present therapeutic pressure applicator and monitoring system is the ease of setting the device to the desired pressure. The applied pressure of the device is displayed as a real-time cushion pressure reading on the screen of a corresponding device. The physician does not have to insert and then remove a pressure gauge, such as one with an inflated pneumatic pad, from between the applicator and the patient so that the true applied pressure is not actually known.

A still further advantage of the present therapeutic pressure applicator and monitoring system is that should the patient inadvertently release the pressure setting fastener set by the physician, such as the Velcro® fastener in the REZA BAND® device, the patient will be able to use the displayed real-time pressure information to accurately reattach the device to the desired pressure level prescribed and set by the physician. The patient need not guess at the applied pressure level and need not schedule a return visit to the physician to reset the pressure.

A still further advantage of the therapeutic pressure applicator and monitoring system is the compact and light weight construction of the pressure applicator and monitoring device. The compact device allows the patients to go about their normal daily lives with as little restriction as possible.

Other aspects and advantages of the invention will become apparent upon making reference to the specification, claims and drawings.

BRIEF DESCRIPTION OF THE DRAWINGS

FIG. 1A is an illustrated view of a conventional band REZA BAND® device secured to the neck of a patient with a detachable pneumatic gauge and inflatable pad used by the treating physician to set the pressure applied to the esophagus at a desired pressure level, and an enlarged view showing the inflatable pad removed.

FIG. 5A is a front view of a fourth disc-shaped embodiment of the therapeutic pressure applicator and monitoring device with a disc-shaped housing.

FIG. 5B is a cross-sectional view of FIG. 5A taken along line 5B-5B showing its disc-shaped housing, internal pressure sensing component and power supply, pressure focusing plate with its central button, and cushion.

FIG. 5C is a cross-sectional view showing the pressure adjusting components moved to an increased pressure position.

DESCRIPTION OF THE PREFERRED EMBODIMENTS

Figure 1B:
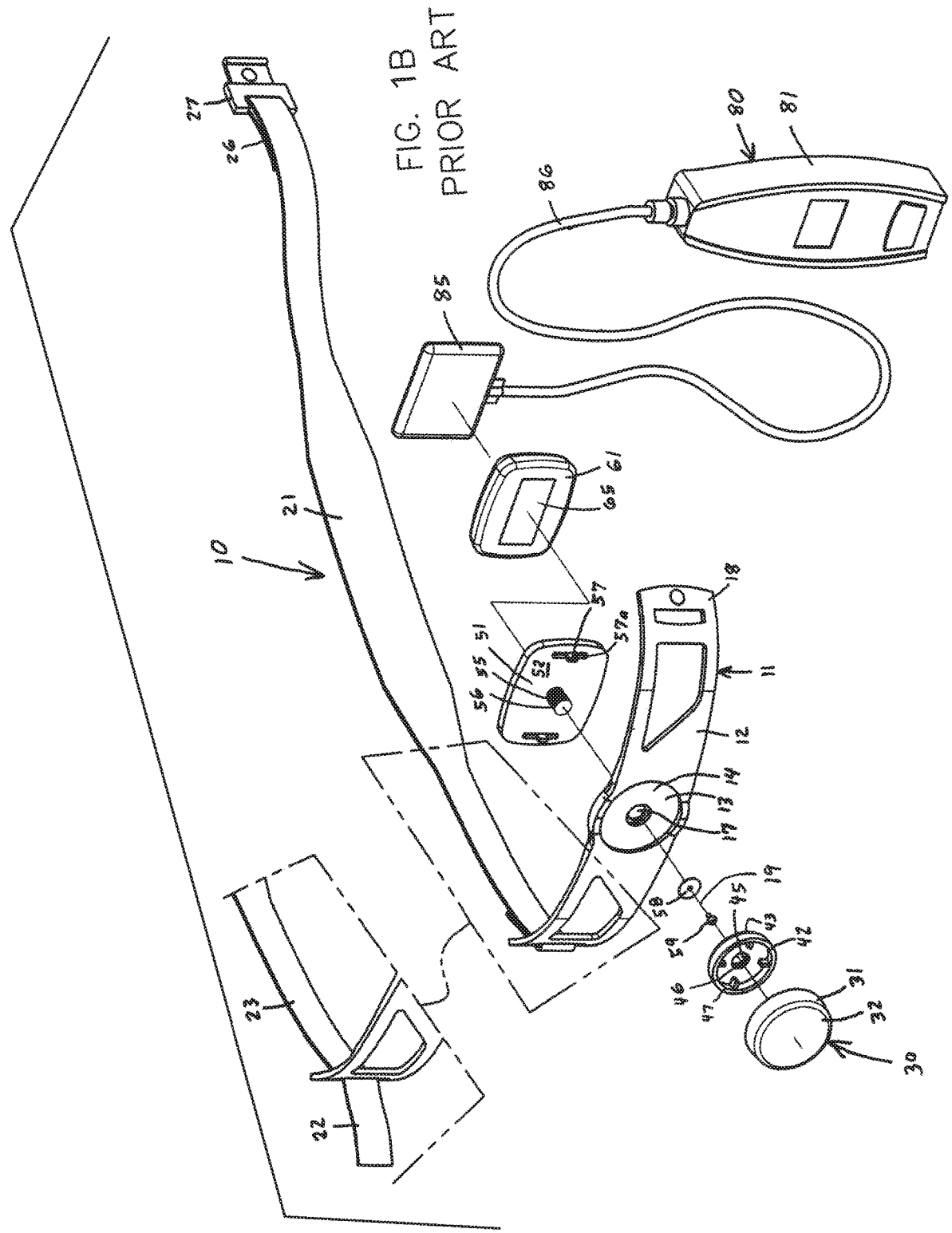
FIG. 1B is an exploded view of the REZA BAND® device showing the strap secured at one end of a semi-flexible strap bracket by a Velcro® fastener and unhooked from the other end by a quick release clip fastener, the device components including the front pressure dial, pressure plate and cushion, as well as the separate pneumatic pad, air tube and pressure gauge.

While this invention is susceptible of embodiments in many different forms, the drawings show and the specification describes in detail preferred embodiments of the invention. It should be understood that the drawings and specification are to be considered an exemplification of the principles of the invention. They are not intended to limit the broad aspects of the invention to the embodiments illustrated.

The present invention pertains to a long-term therapeutic pressure applicator and monitoring device generally indicated by reference numbers 100 and a real-time pressure monitoring system generally represented by reference number 200 as shown in FIGS. 2-11. The therapeutic pressure applicator and monitoring device 100 has a securing member or mechanism 101 to secure a pressure adjusting mechanism 105 to the patient 5. Depending on the body part involved, the securement member or mechanism 101 can take a variety of forms. In a first embodiment, the therapeutic pressure applicator and monitoring device 100 is secured to the neck 7 to reduce esophageal reflux as in FIGS. 2A-J. The securing mechanism 101 is the conventional REZA BAND® device 11 used by the treating physician to apply an approximate pressure to the patient that is close to the desired pressure. As noted above, the band 11 has the semi-flexible strap or securement bracket 12 with its central recess 13, front and rear sides surfaces 14 and 15 and opening 17.

Figure 2A:
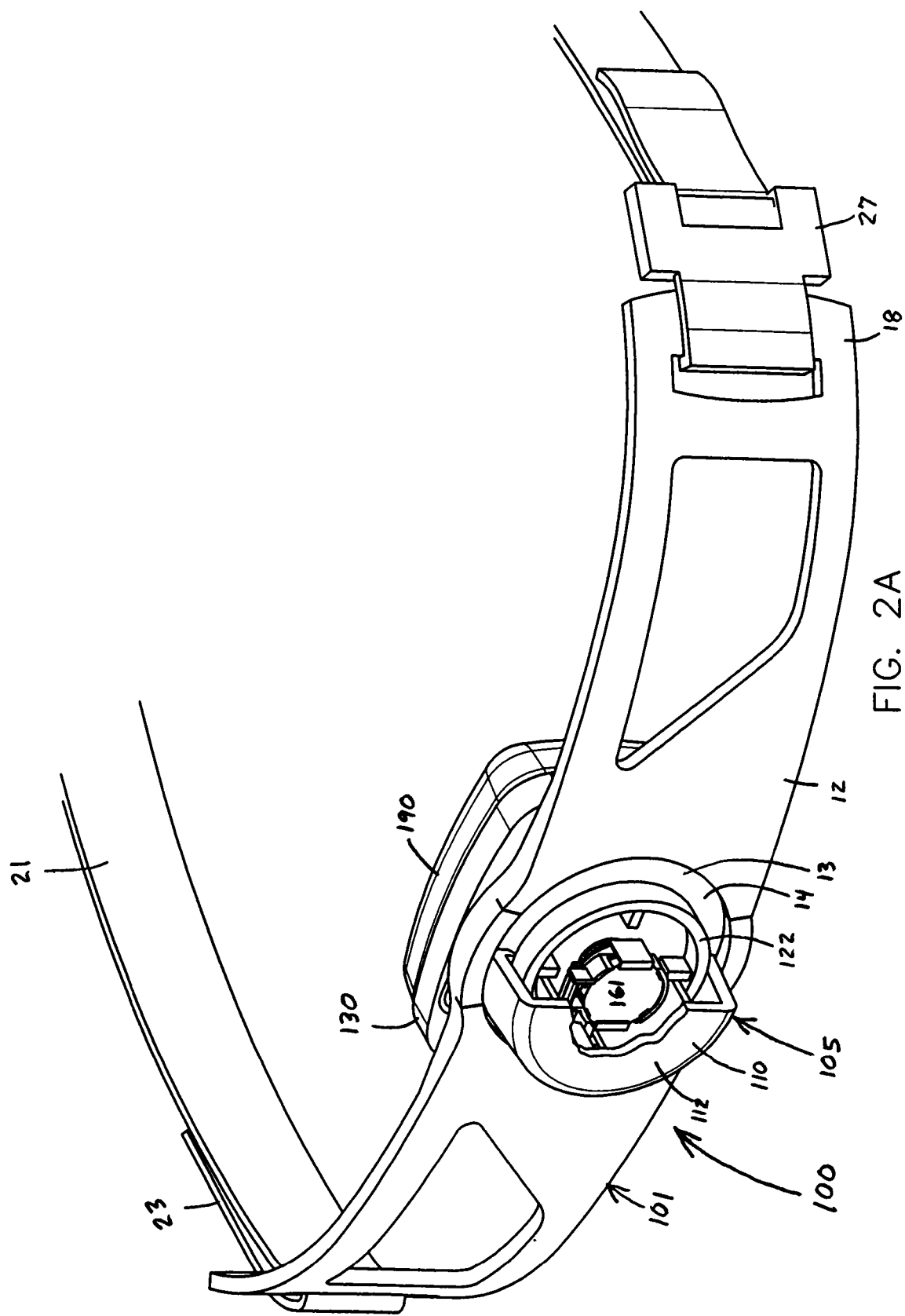
FIG. 2A is a perspective view of the first embodiment of the present therapeutic pressure applicator and monitoring device with the pressure dial partially cut away to show the power supply secured to the central post of the pressure sensing component.
Figure 2B:
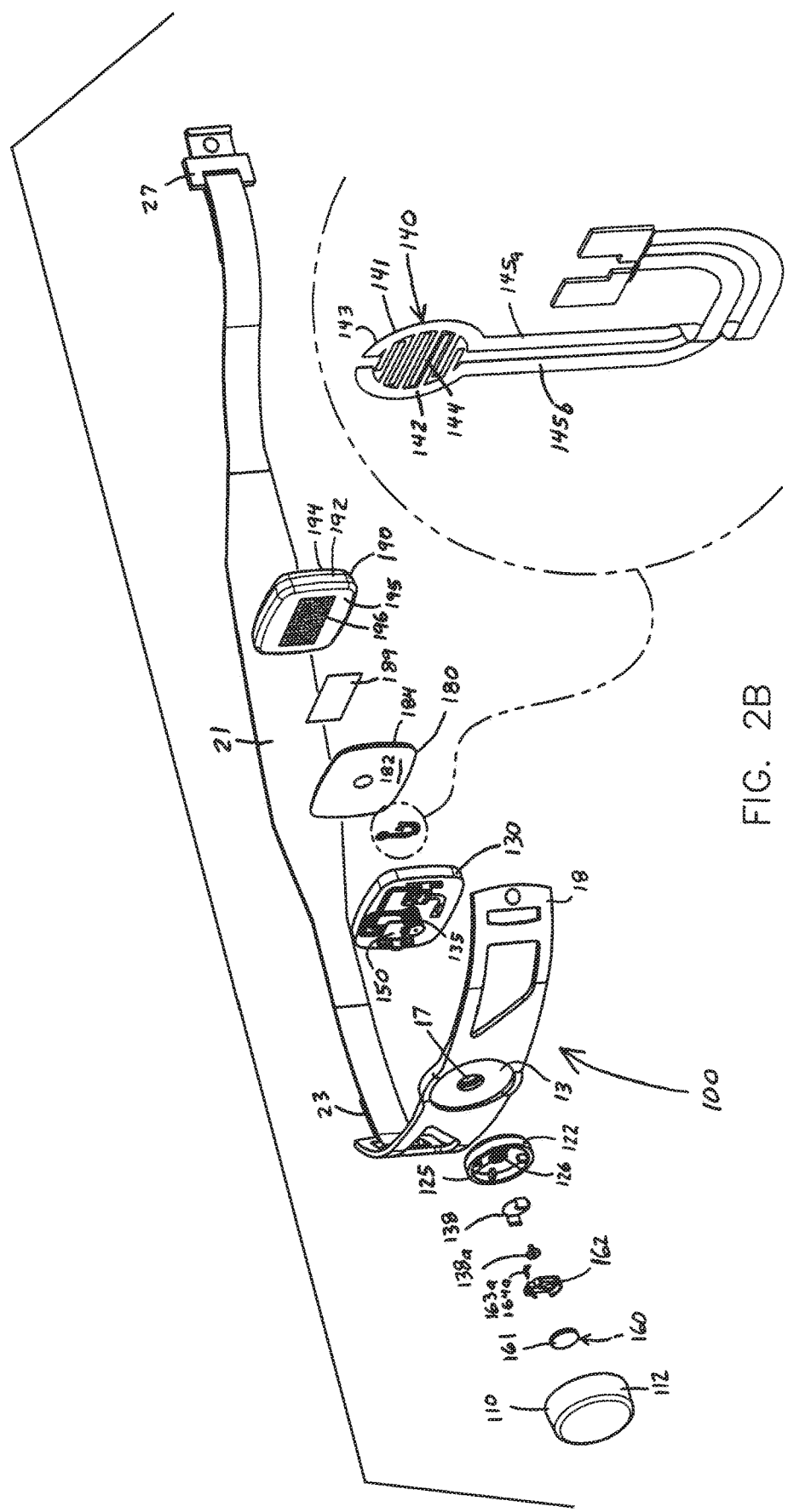
FIG. 2B is an exploded view of the first embodiment showing a pressure adjusting knob with an internal battery, pressure sensing component with a computer module, memory and transceiver, a pressure gauge with a force-sensing sensor, pressure focusing plate with a central button aligned over the sensor, and cushion with its Velcro® securement strip, and further showing the conventional neck band having a molded securement bracket with a strap secured at one end to the bracket by a Velcro® fastener and to the other end by a clip.
Figure 2C:
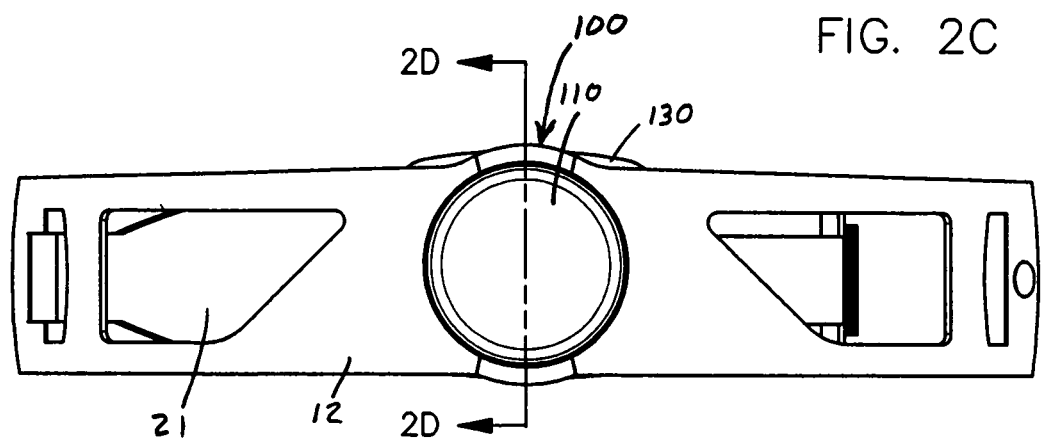
FIG. 2C is a front view of the first embodiment.
Figure 2D:
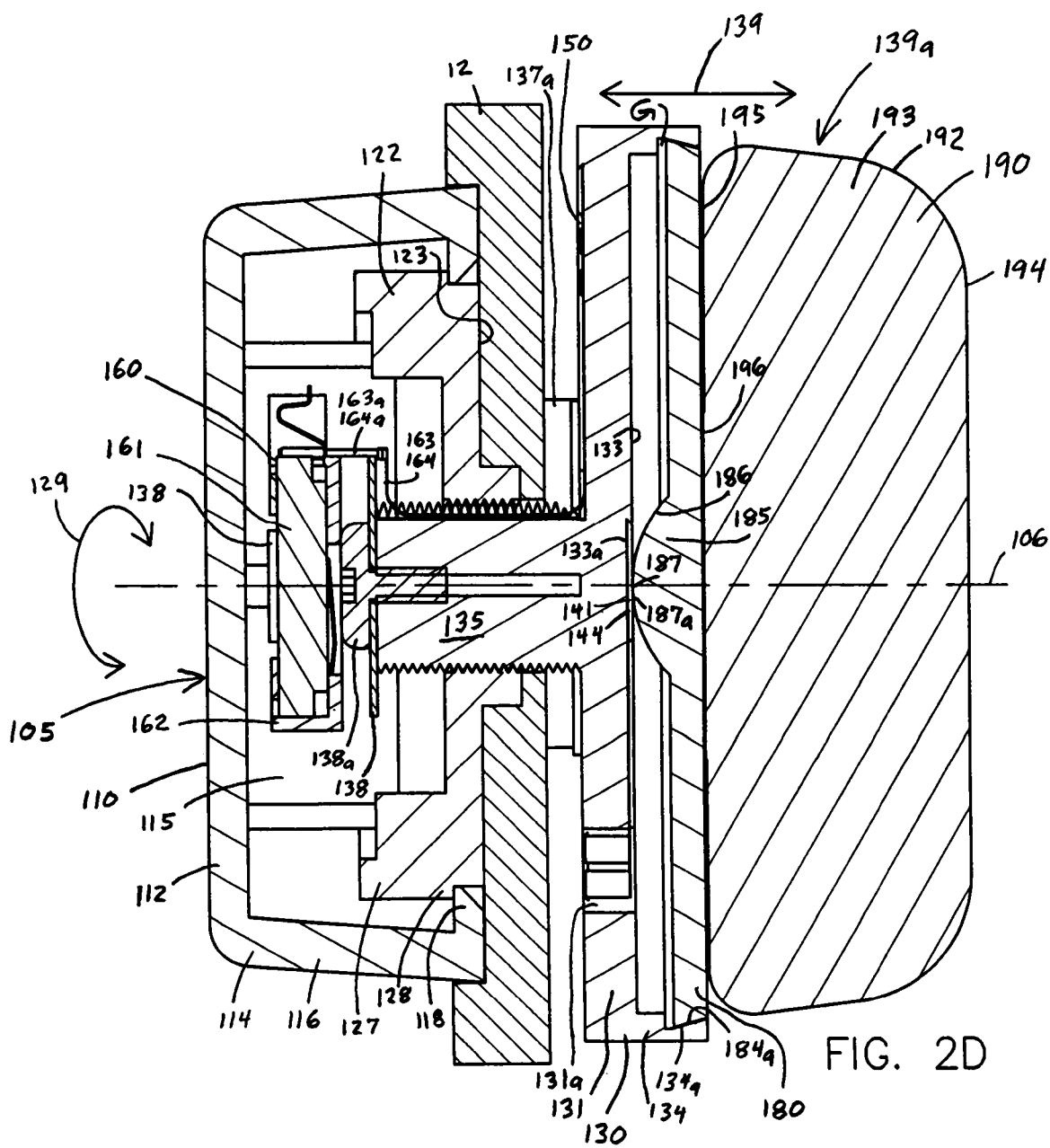
FIG. 2D is a cross-sectional view of the first embodiment shown in FIG. 2C taken along line 2D-2D, and showing the pressure adjusting knob with an internal battery secured to a threaded central post of the pressure sensing component, the central curved button of the pressure focusing plate aligned in pressing engagement with the pressure sensor secured in a recess of the sensing component, the cushion, and the conventional securement bracket of the neck band.
Figure 2E:
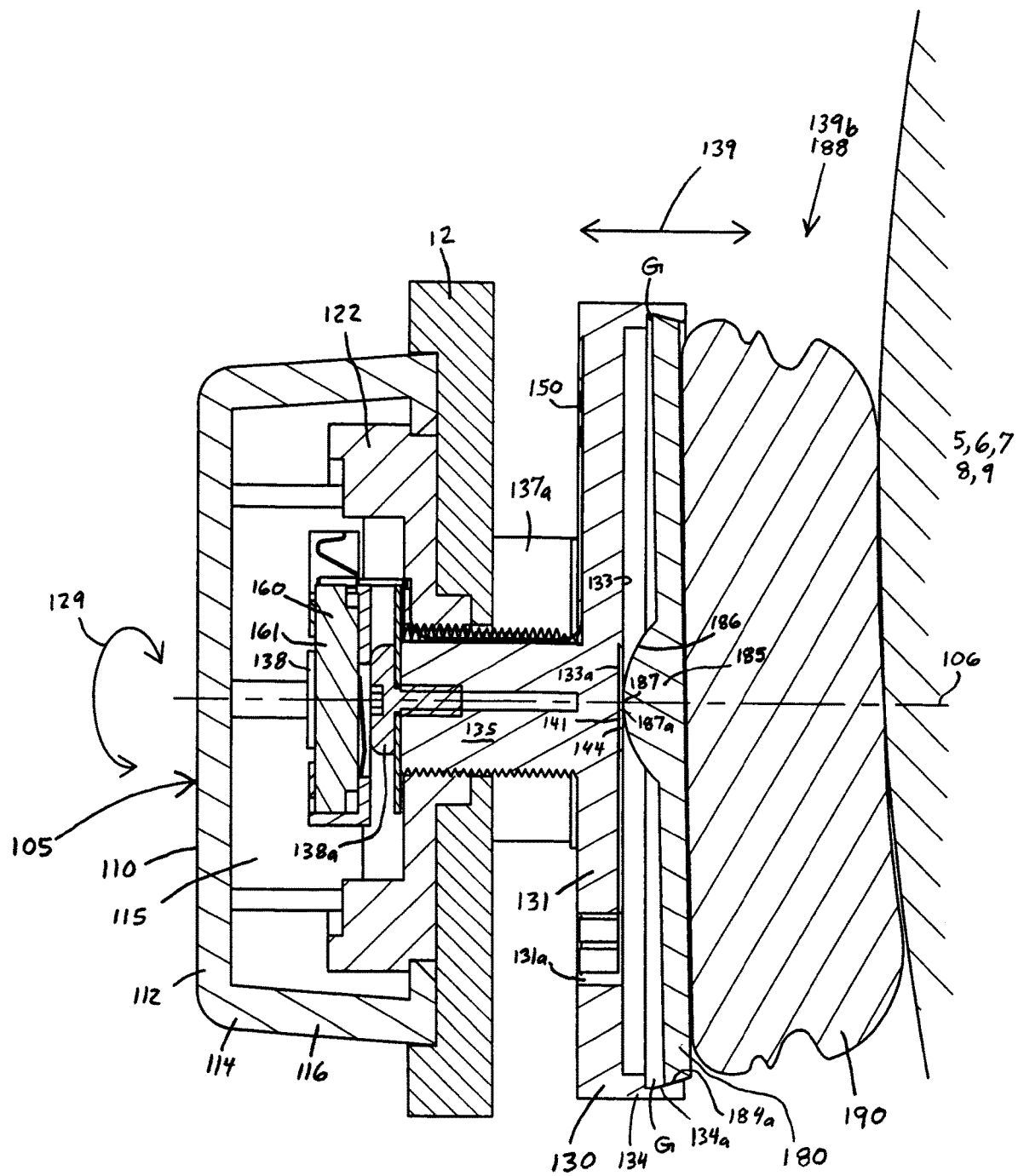
FIG. 2E is a cross-sectional view of the first embodiment shown in FIG. 2D showing the pressure adjusting components moved to an increased pressure position and with the focusing plate slightly rotated.
Figure 6:
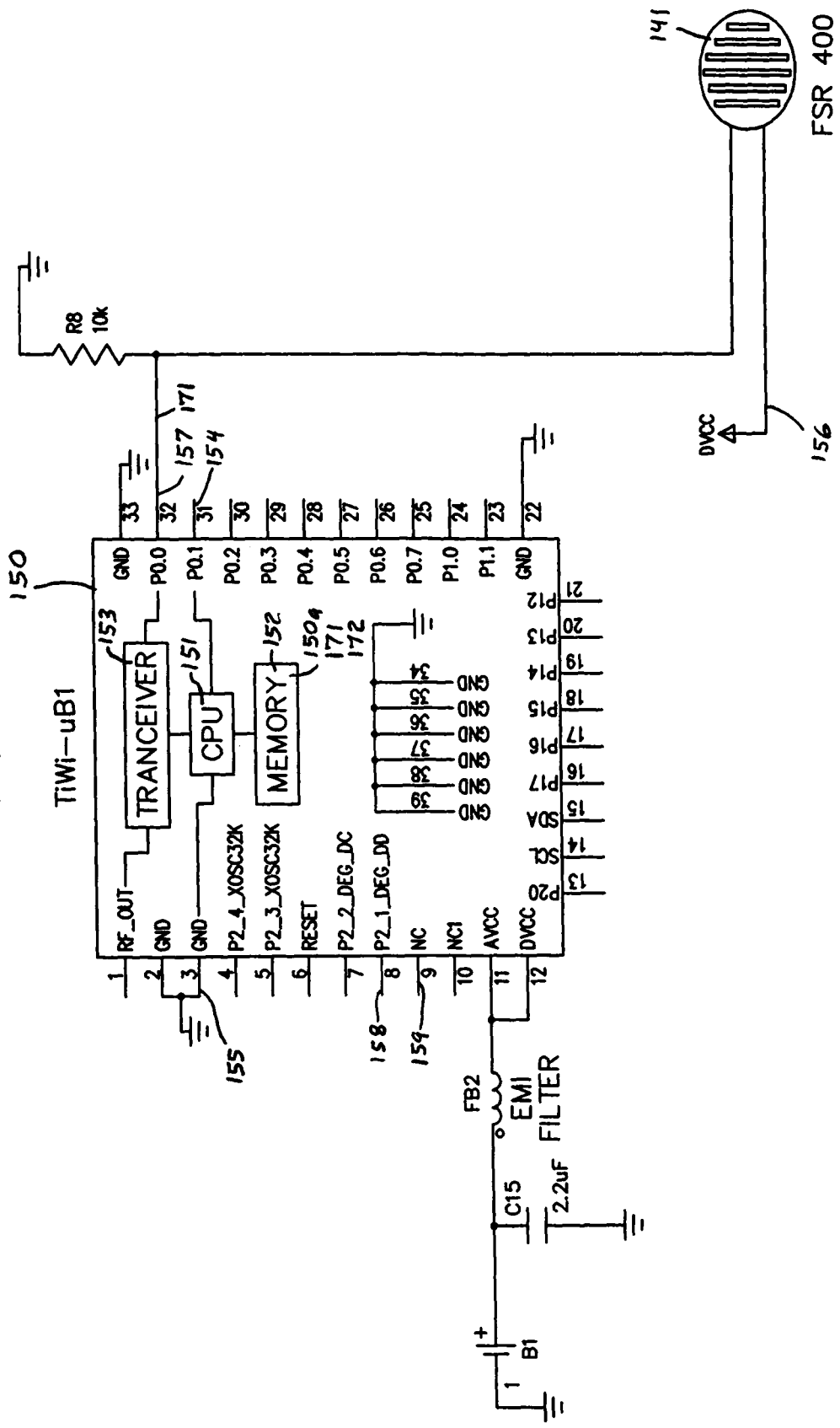
FIG. 6 is a schematic view of the computer module and pressure sensor of the present invention.

The pressure adjusting mechanism 105 adjusts the amount of pressure applied to the body part of the patient 5 to obtain the desired or prescribed pressure by the treating physician. As shown in FIGS. 2C and 2E, the pressure adjusting mechanism 105 includes a pressure adjusting dial 110, pressure sensing component 130, pressure gauge 140, computer module 150, power supply 160, pressure focusing plate 180 and cushion 190. As shown in FIG. 6, the computer module 150 has an internal CPU 151, memory 152 and transceiver 153 to obtain, store and transmit long-term, real-time cushion pressure data 172. The pressure adjusting mechanism 105 has a depth from the strap bracket 12 to the rear surface of the cushion 190 of about 0.375 of an inch, which is substantially the same as the depth of the REZA BAND® device 10.

The pressure adjusting dial 110 is formed by a knob 112 and a base 122. The dial 110 is located on the front side 14 of securement bracket 12 facing away from the body part. The knob 112 has a semi-circular outer shell 114 to form an interior chamber 115. The rear end of the knob 112 forms a rim 116 with inwardly extending tabs 118. The dial 110 also has a circular base 122 that is flushly and rotatably received by a circular recess 13 of the strap bracket 12. The circular base 122 has a rear surface 123 and a central opening 125 formed by a threaded sidewall 126. The rim 116 of the knob 112 is firmly joined to a rim 127 of the base 122. The rim 127 of the base 122 has tabs 128 that mate with tabs 118 of the knob 112 so that the knob and base rotate 129 in unison.

Figure 2F:
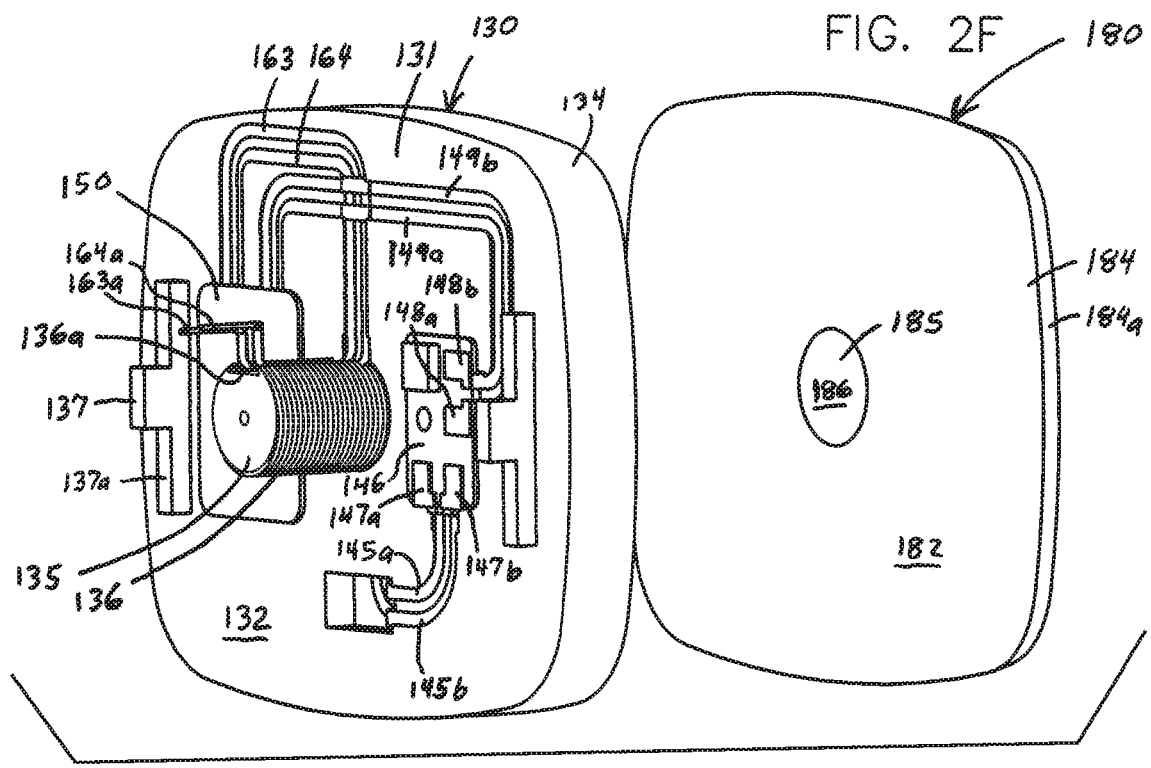
FIG. 2F is an exploded view showing the front sides of the pressure sensing component and pressure focusing plate, the pressure gauge and computer module mounted to the pressure sensing component, the leads and terminals electrically connecting the sensor to the computer module, and the computer module leads routed through a channel in the central post of the sensing component for electrical communication with the battery.
Figure 2G:
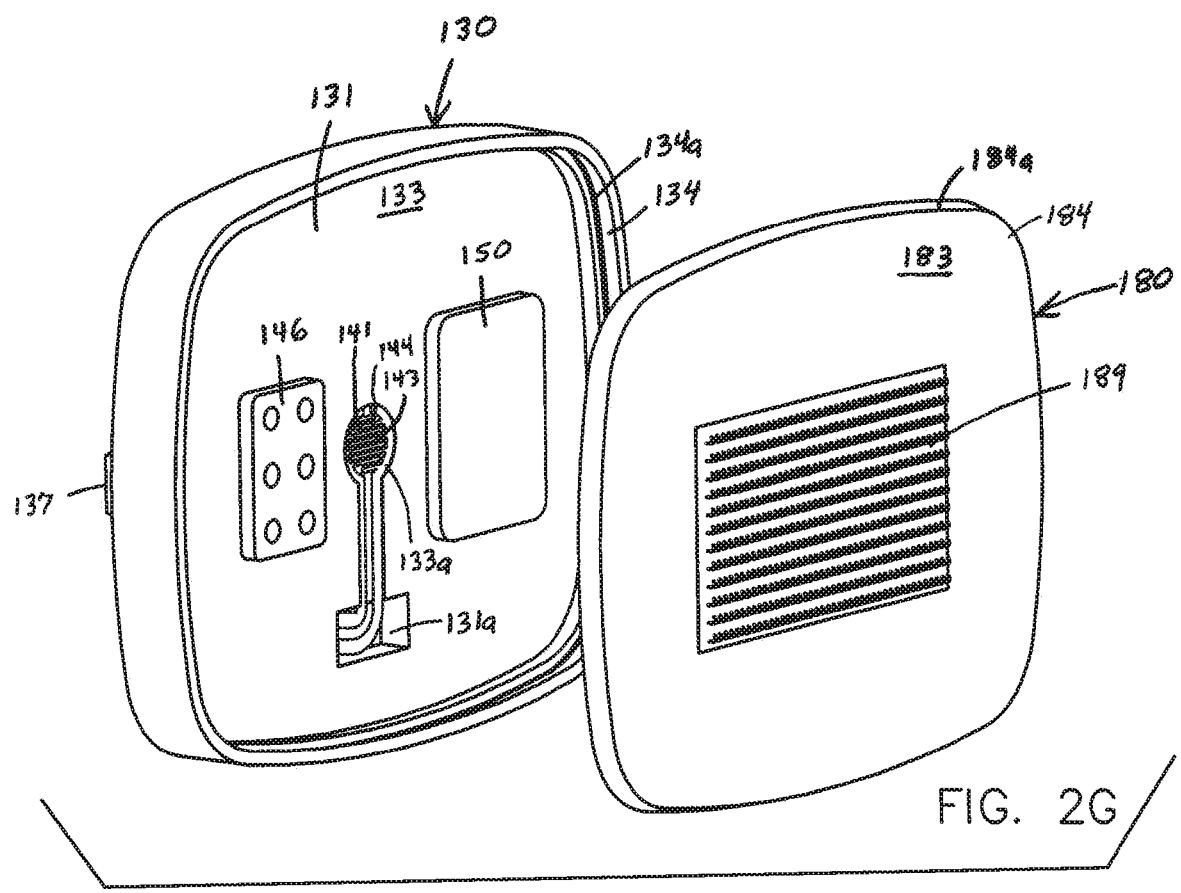
FIG. 2G is an exploded view showing the rear sides of the pressure sensing component and pressure focusing plate, the computer module and sensor and its base mounted to the pressure sensing component, and the Velcro® securement strip on front surface of the pressure focusing plate.
Figure 2H:
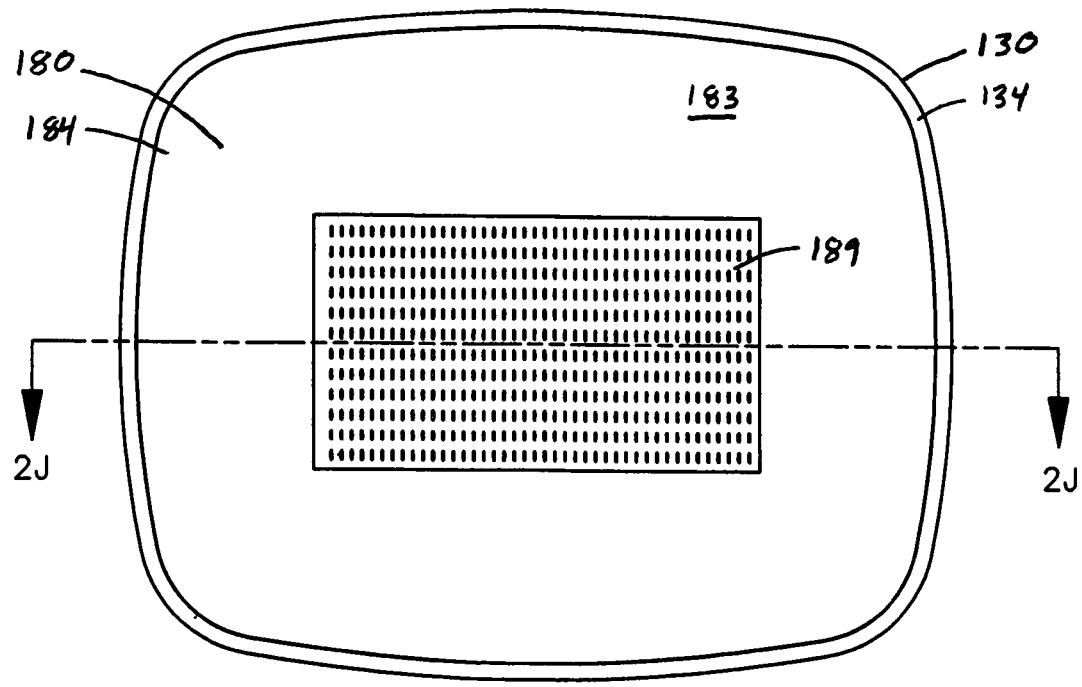
FIG. 2H is an elevated view showing the pressure focusing plate secured to the rim of the pressure sensing component.
Figure 2J:
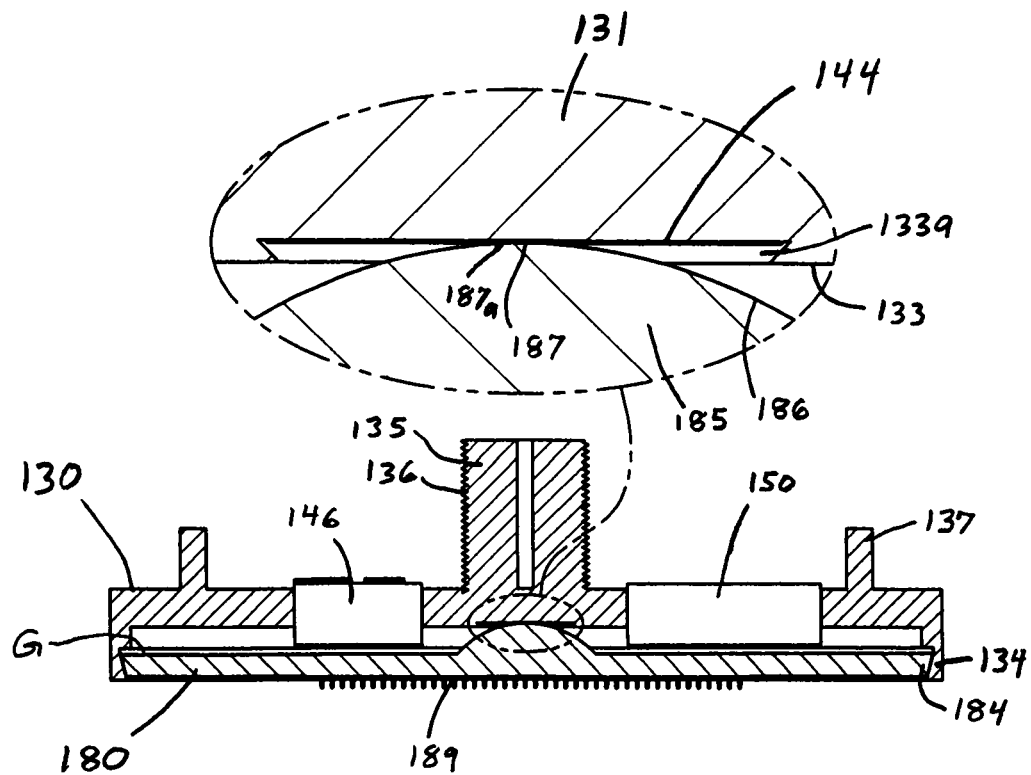
FIG. 2J is a cross-sectional view of FIG. 2H taken along line 2J-2J showing the pressure focusing plate received in and held by the rim of the pressure sensing component with the pressure button in linear alignment with the force-sensing sensor and pressure adjusting post, and showing an enlarged view of the curved surface of the central button engaging the flat surface of the force-sensing sensor.

The pressure sensing component 130 is rigid and preferably made of conventional Acrylonitrile butadiene styrene (ABS) plastic with a tensile strength of 6,600 pounds per square inch (psi). The dial 110 and sensing component 130 engage opposite sides of the strap bracket 12. The sensing component 130 is located on the rear side 15 of securing bracket 12 facing toward the body part. The sensing component 130 has main body 131 with front and rear surfaces 132 and 133 and a thickness of about 0.25 inches. The rear surface 133 has a central recess 133a. The sensing component 130 and its main body 131 have a generally rectangular shape with a length of about 1.625 inches and a height or width of about 1.25 inches, which are the same as the REZA BAND® device. An outer rearwardly projecting tubular rim 134 with a length of about 0.1 of an inch extends from the rear surface 133 around the perimeter of the main body 131. The radial mounting rim or tubular perimeter rim 134 has an end with an inwardly facing securement notch 134a that extends around the circumference of the rim. The radial notch 134a has an inwardly sloped or angled cross-sectional shape as best shown in FIGS. 2D, 2E and 2J.

The pressure sensing component 130 has a central post or stem 135 with a threaded sidewall 136 that extends from its front surface 132. The forward extending stem 135 has a length of about 0.375 inches and a diameter of about 0.25 inches. The threaded stem 135 extends unobstructedly through the larger diameter, unthreaded opening 17 in the strap bracket 12. The threaded sidewall 136 of the stem 135 is in mating threaded engagement with the threaded sidewall 126 forming the central opening 125 of the dial base 122. The main body 131 has three openings. One opening is sized to matingly receive a computer module and another opening is sized to matingly receive a base of a force sensor. The third opening 131a is used to rout the sensor leads as discussed below. The threaded sidewall 136 has a relatively small cut away portion extending from the top of the post 135 to its base to form a channel 136a for routing the power supply 160 wires as discussed below.

The pressure sensing component 130 is rotationally fixed to the strap bracket 12, and does not rotate with the pressure dial 110. The sensing component 130 has two forward extending mounting or securement posts 137. The posts 137 extend from front surface 132, straddle the stem 135 and are generally parallel to the stem. The posts 137 are flushly received by the anti-rotation slots 15a of the strap bracket 12 to secure the sensing component 130 to the dial bracket 12. The tips of the posts 137 are flared so that they snap-fit into the slots 15a and do not become dislodged from the slots during use. The posts 137 have shoulders 137a that form limit stops for the retraction of the plate 130.

A battery hold down clip 138 is secured by a screw fastener 138a to the flat surface at the forward end or top of the stem 135. The pressure adjusting dial 110 rotates about the threaded stem 135 to extend or retract the sensing component 130 along a linear path of travel 139 between decreased and increased pressure positions 139a and 139b. The diameter of the clip 138 is larger than that of the stem 135 and central opening 17 of the strap bracket 12 to form a limit stop that prevents the overextension of the sensing component 130 into the neck 7 of the patient 5. The channel 136a and battery wires do not interfere with the rotatable threaded engagement between the stem 135 and dial base opening 125, or the longitudinal movement 139 of the sensing component 130 when the dial 110 is rotated 129.

The pressure gauge 140 has a force-sensing sensor 141 configured to collect electrical data associated with the pressure applied by the cushion to the patient. The sensor has a flat front and rear surfaces 142 and 143. The sensor 141 is relatively thin with a thickness of about 0.012 inches, and has a generally circular sensing area 144 with a diameter of about 0.25 inches. The front surface 142 of the sensor 141 is in flush engagement with the rear surface 133 of the central recess 133a of the sensing component 130. The sensing area 144 is centrally located on the sensing component 130 and along the centerline 106 of the device 100.

The sensing area 144 includes electrically conductive spaced input and output contacts that are electrically connected to input and output sensor leads 145a and 145b. The sensor 141 is preferably a force-sensing sensing resister, such as the Model FSR 400 manufactured by Interlink Electronics. The material between the contacts of the sensor is preferably a polymer thick film (PTF) that exhibits a decrease in electrical resistance when an increase in force or pressure is applied to its surfaces 142 and 143. When a force is applied to the rear surface 143 of the working area 144 of the sensor 141, the material between the sensor contacts is compressed against rear surface 133 of the sensing component 130. The change in resistance continues as long as the force or pressure is applied so that the sensor continually measures the force or pressure being applied to the sensor. The change in resistance of the material caused by the compression of the sensor 141 is converted into an electrical output signal such as a change in voltage or current. This sensor output signal includes focused cushion pressure data 171.

The pressure gauge 140 has a base 146 to mount the sensor 141 to the main body 131 of the pressure sensing component 130. To maintain the compact nature of the pressure applicator 100 and adjusting device 105, the base 146 fits predominantly within the main body 131 and does not extend beyond the forward edge of the rim notch 134a as best shown in FIGS. 2G and 2J. The sensor leads 145a and 145b are in electrical communication with the spaced input and output sensor contacts, respectively, travel through the recess 133a along the rear side 133 of the main body 131, and pass through the base opening 131a. The input and output sensor leads 145a and 145b plug into and are in electrical communication with the input and output terminals 147a and 147b of the base 146, respectively, as shown in FIG. 2F. Base input and output terminals 147a and 147b are in electrical communication with base input and output terminals 148a and 148b, respectively. Similarly, base terminals 148a and 148b are in electrical communication with base input and output leads 149a and 149b, respectively, to electrically connect the sensor 141 to the computer module 150. The leads and terminals 145, 147, 148 and 149 are generally flush with the front surface 132 of the main body 131.

The computer module 150 has an integrated programmable microcontroller or central processing unit (CPU) 151, memory 152 and transceiver 153 that are internal to the module as shown in FIG. 6. These components are in electrical communication via its internal circuitry. The processor 151 is programmed or otherwise configured to provide the functionality described herein, and is specifically programmed or configured to collect focused cushion pressure data 171 from sensor 140, process that data into cushion pressure data 172, store the data 171 and 172 in its memory 152, and transmit the data 171 and 172 as a pressure data signal via transceiver 153. The module 150 is preferably manufactured by LSR as a compact TiWi-uB1 Bluetooth Smart module with a low-power 2.4 GHz Bluetooth 4.0 (BLE) System-on-Chip (SoC) with an integrated microcontroller, embedded flash memory, and Texas Instruments CC2541 transceiver with RF output power and dipole antennas with a range of about 10 feet. The module 150 has a thickness of about 0.125 inches, and is generally rectangular in shape with a width of 0.5 inches and a length of 0.75 inches. Communications with other devices via the transceiver 153 can be wireless, radio frequency messages that provide the real-time cushion pressure data 172.

To maintain the compact nature of the pressure applicator 100 and adjusting device 105, the module 150 is mounted predominantly within the main body 131 of the pressure sensing component 130, and does not extend beyond the forward edge of the rim notch 134a as best shown in FIGS. 2G and 2J. The module 150 includes module power input and output terminals 154 and 155 and pressure gauge input and output terminals 156 and 157 as shown in FIGS. 2B, 2F and 6. The module 150 also has additional input and output terminals 158 and 159 for an optional automated embodiment discussed below. The pressure gauge leads 149a and 149b are connected to the input and output terminals 156 and 157, respectively, so that the pressure gauge 140 is in electrical communication with the computer module 150 and its CPU 151.

A battery 161 provides the power supply 160 to the computer module 150 to operate the programmed CPU 151, transceiver 153 and pressure gauge 140. The battery 161 is preferably a conventional CR1025 lithium coin cell or button cell battery with a capacity of about 30 mAh to provide a year of useful life for the device 100. The coin-shaped battery 131 is located in the dial knob chamber 115, and is held by an electrical interface casing 162. The securement prongs of the clip 138 secure both the battery 161 and casing 162 to the clip. The battery 161 and casing 162 are held by the clip 138 at the top of the stem 135. The clip 138, battery 161 and casing 162 remain rotationally fixed on the stem 135, and do not rotate with the knob 112. The battery casing 162 has positive and negative leads 163 and 164 connected to the positive and negative terminals on the battery 161, respectively. The battery 161 can be replaced as needed by temporarily removing the knob 112 to access the battery. The battery 161 is in electrical communication with the computer module 150 as shown in FIGS. 2E, 2F and 6. The battery casing leads 163 and 164 extend from the terminals 163a and 164a of the battery casing 162 in the dial knob chamber 115, through the stem channel 136a and into engagement with the positive and negative computer module terminals 154 and 155.

The computer module 150 uses the pressure gauge 140 to gather long-term, real-time cushion pressure data 172. The CPU 151 is programmed to periodically send an input signal to the pressure gauge 140 via leads and terminals 145a, 147a, 148a, 149a and 156. Based on the real-time focused cushion pressure exerted on the working area 144 of the sensor 141, the sensor sends an output signal with real-time focused cushion pressure data 171 back to the CPU 151 via leads and terminals 145b, 147b, 148b, 149b and 157. As noted above and discussed more fully below, the pressure applied by the cushion 190 to the rear surface of the pressure focusing plate 180 is focused or collected onto a small contact area or zone of the button 185 actually pressing against the sensor 141, so that the corresponding small contact area or zone of the sensor experiences a much larger force or pressure than any one spot on the cushion. The programming of the CPU 151 converts the focused cushion pressure data 171 into real-time cushion pressure data 172 corresponding to the actual pressure between the cushion 190 and the patient 5 at a given point in time. The CPU 151 is programmed to add time and date information to the real-time cushion pressure data 172 and continuously store that pressure data 172 in its memory 152. The CPU 151 is programmed to format or otherwise process the output signal data 171 obtained by the sensor 140 into formatted real-time cushion pressure data 172 that is readily received and processed by other devices 210 in the system 200. As discussed below, the CPU 151 is further programmed to periodically transmit the long-term, real-time pressure date data 172 stored in its memory 152 via its transceiver 153 to an external device 210 in the monitoring system 200.

The pressure focusing plate 180 is rigid and preferably made of ABS plastic with a tensile strength of 6,600 psi. The plate 180 is thin and fits within the rim 154 of the pressure sensing component 130. The focusing plate 180 has front and rear sides or surfaces 182 and 183 and a perimeter 184. The plate 180 has a generally rectangular shape with a width and a length substantially equal to those of the main body 131. The rear surface 183 has a surface area of about two square inches. The perimeter 184 has an inwardly angled edge 184a. The focusing plate 180 snap fits into secure engagement with the rim 134 of the sensing component 130. The angled edge 184a is matingly received by the inwardly angled notch 134a of the sensing component rim 134 around the entire perimeter of the focusing plate 180 to secure the focusing plate to the sensing component 130.

The sensing component 130 and sensing plate 180 are structures to focus the forces distributed along the surface of the cushion 190 onto a contact area of the sensor 141. The length and depth of the angled notch 134a, the thickness of the focusing plate 180, and outward projection of the button 185 are sized so that there is a gap G between the flat front surface 182 around the perimeter 184 of the focusing plate 180 and the forward lip of the notch 134a as shown in FIGS. 2E and 2J. The gap G extends completely around the perimeter 184 of the pressure focusing plate 180 so that pressure exerted on the focusing plate 180 by the cushion 190 is transmitted through the button 185, and is not supported by the rim 134 of the control sensing component 130. The front end of the notch 134a is in spaced planar or parallel relation to the rear surface 133 of the main body 131 of the sensing component 130. The notch 134a is spaced from the main body rear surface 133 the so that the forward most point or apex 187 of the curved button 185 engages the sensor 141 while maintaining the perimeter gap G between the focusing plate 180 and the forward lip of the sensing component notch 134a. The flared outer portion of the rim 134 forming the notch 134a combines with the angled outer edge 184a of the pressure focusing plate 180 to assist in maintaining the engagement of the button 185 against the sensor 141 while maintaining the perimeter gap G around the plate 180.

The central button 185 of the pressure focusing plate 180 is aligned over the working area 144 of the force-sensing sensor 141 as shown in FIGS. 2E and 2J. The front surface 186 of the button 185 has an outwardly curved or convex shape, preferably having a uniform radius of 0.125 inches. The apex 187 of the curved surface 186 is preferably positioned to engage the middle of the sensor 141. The apex 187 of the button 185 is located at the center of the focusing plate 185 and along the centerline 106 of the device 100. The only part of the focusing plate 180 supporting the compression load or pressure exerted by the cushion 190 on the neck 7 of the patient 5 is the button 185, which presses against the force sensor 141 laying flat against the rear surface 143 of the pressure sensing component 130. The load or pressure exerted by the cushion 190 across the rear surface 133 of the rigid focusing plate 180 is focused or amplified into a larger load or pressure exerted by the curved contact area 187a of the central button 185 onto the sensor 141. Naturally, the size of the button contact area 187a and the size of the sensor contact area are the same.

The contact area 187a of the compressed sensor 141 around the curved apex 187 button 185 is believed to be slightly curved and small, and not merely point contact.

While the gauge 140 is stated to be a pressure gauge, it should be understood that the sensor 141 measures the force or pressure applied by the contact area 187a of the curved button surface 186 on the generally flat sensor surface 143. The distributed pressure load applied by the cushion 190 to the relatively large rear surface 183 of the pressure focusing plate 180 is focused or amplified into a much larger force or focused cushion pressure applied by the relatively small contact area 187a of the curved button surface 186 onto the compressed contact area of the surface 143 of the sensor 141.

Given the rounded shape of most parts of the human body, the perimeter gap G of the focusing plate 180 is uniform around the circumference of the mounting rim 134 in most securement situations as shown in FIG. 2J. This is because the pressure exerted by the cushion 190 across the rear surface 183 of the focusing plate 180 should be substantially evenly distributed relative the center 106 of the focusing plate 140. However, in situations where the pressure exerted by the cushion 190 across the focusing plate 180 is not evenly distributed about the center 106 of the focusing plate 180, such as by an anomaly in the body structure due to a scar, cyst, or underlying bone or cartilage, then the curved surface 186 of the button 185 is free to rock or rotate slightly to a position 188 where the gap G around the perimeter of the focusing plate 180 is not uniform as shown in FIG. 2E. Because the button front surface 186 has a uniform curvature, the contact area 187a between the button 185 and the working area 144 of the sensor 141 remains unchanged even with the rotation of the plate 180. Thus, a shift in the pressure distribution relative to the centerline 106 of the device 100 and focusing plate 180 does not result in a fluctuation in the pressure reading observed by the sensor 140. To accommodate the rocking movement 188a of the focusing plate 180, a small gap of about two millimeters (not shown) is provided between the angled end surface 184a of the plate 180 and the angled surface of the notch 134a.

The uniformly curved button surface 186 results in more stable real-time cushion pressure readings 172 observed by the sensor 140, device 100 and monitoring system 200. Although the button 185 could have a flat raised surface with side edges, such a structure could destabilize the real-time cushion pressure readings 172 observed by the sensor 140. Situations involving a shift in the cushion pressure distribution across the focusing plate 180 so that the pressure distribution is unevenly distributed about the centerline 106, can result in the flat raised button 185 riding up on its side edge. This would cause a significant contraction in the contact area 187a between the button 185 and sensor 140, which would result in the sensor 140 observing a false spike or increase in real-time cushion pressure when only a shift in the cushion pressure distribution about the center 106 occurred.

The cushion 190 has an outer woven fabric 192 and an inner resilient foam material 193. The cushion 190 has front and rear sides or surfaces 194 and 195, and is secured by a pair of Velcro® strips 189, 196 to the rear surface 53 of the pressure focusing plate 180. The cushion 190 is relatively soft or deformable and resilient, and its foam material is preferably made of Neoprene SCE-41. The rear surface 194 of the deformable and resilient cushion 190 conforms to the shape of the body of the patient 5, and helps evenly distribute the pressure applied across the rear surface 194 of the cushion 190 to alleviate uncomfortable pressure points between the device 100 and the soft tissue of the throat and neck 7, and helps keep the pressure adjusting mechanism 105 properly positioned on the neck or body. The pressure load is supported by and distributed across front surface 195 of the cushion 190, which in turn transfers the distributed pressure load to the rear surface 183 of the focusing plate 180. The lengths and widths of the cushion 190, focusing plate 180 and sensing component 130 are sized so that their outer ends or perimeters are in aligned registry. The cushion 190, pressure focusing plate 180 and its button 185, sensor 141 and its working area 144, pressure sensing component 130 and its stem 135 and dial 110 of the pressure adjusting mechanism 105 are all centrally aligned on and are generally symmetrical about the central axis 106 of the device 100. The cushion 190 is removable so it can be periodically washed or replaced during the long term use of the applicator 100.

When the dial 110 is rotated 29 to increase the amount the cushion 190 is compressed into the neck 7 or body of the patient 5, the cushion pressure exerted on the body increases and this increase is transmitted to the pressure focusing plate 180. The pressure exerted by the cushion 190 on the patient 5 is transmitted through the button 185 and sensor 141 to the pressure sensing component 130, and to the securement mechanism 101, such as the neck band 11 and bracket 12. As the real-time cushion pressure exerted on the neck 7 changes due to the rotation of the dial 110 or swelling of the body, the real-time cushion pressure data 172 collected by the computer module 150 changes.

Figure 1C:
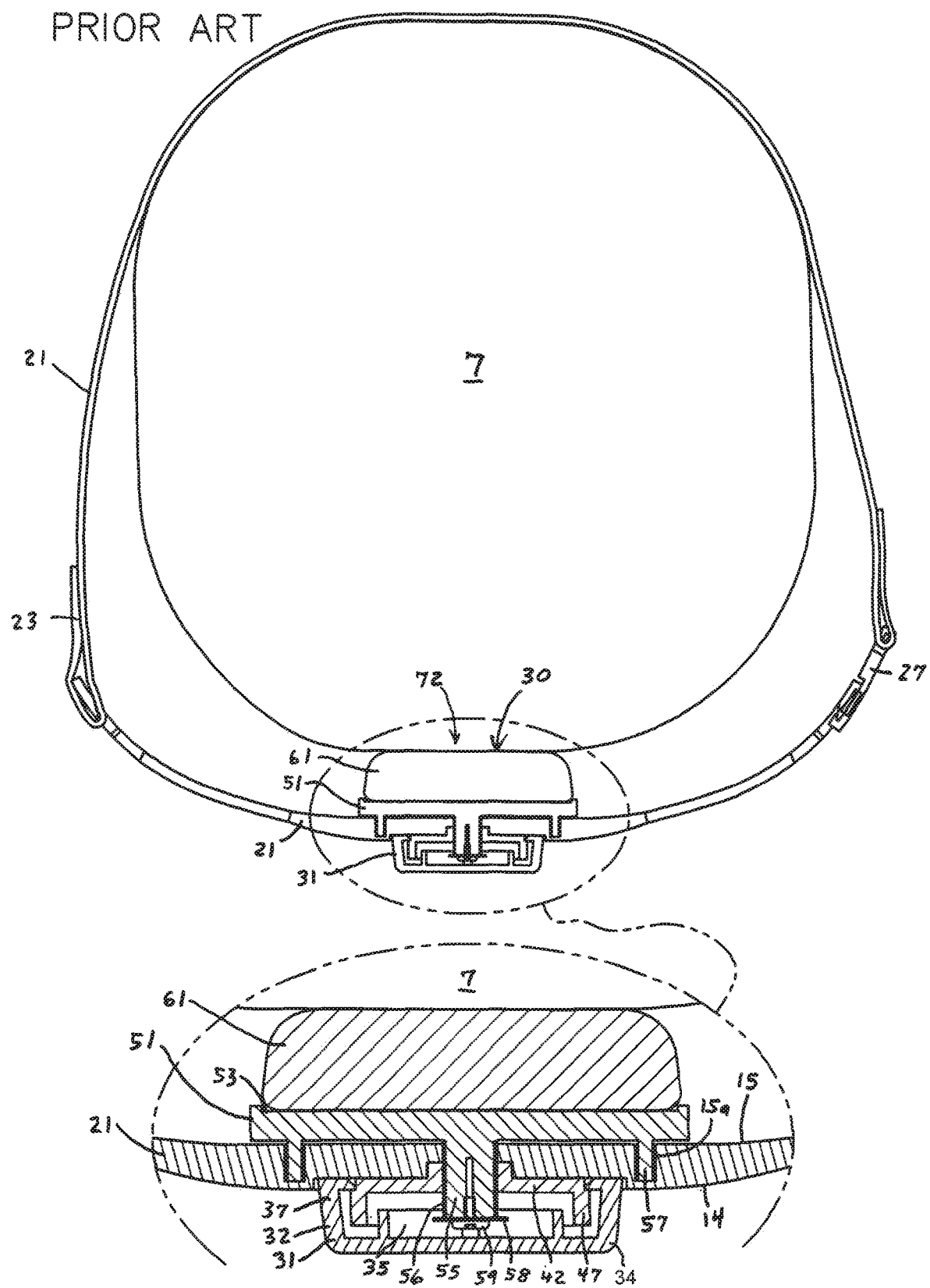
FIG. 1C is a top view of the REZA BAND® device secured around the neck of a patient and showing a cross-sectional view of the pressure plate in a rearward position.
Figure 1D:
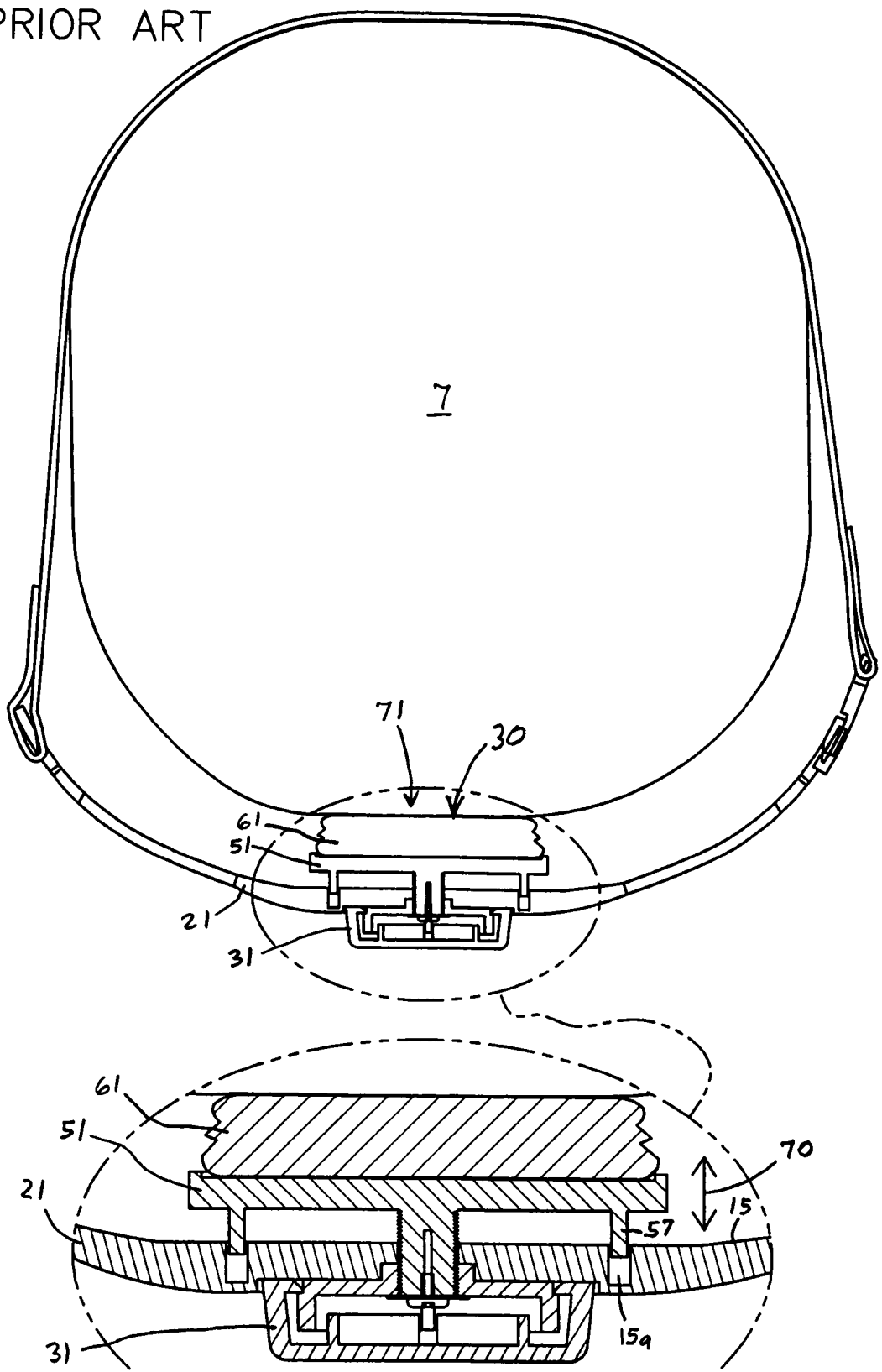
FIG. 1D is a top view of the REZA BAND® device secured around the neck of a patient and showing a cross-sectional view of the pressure plate advanced to a forward position to increase the pressure applied to the neck and showing the flexing of the strap bracket.

The treating physician secures the long-term therapeutic pressure applicator 100 to the patient 5 in two steps. First, with the clip 27 secured, the treating physician selectively positions and secures the Velcro® fastener 23 to achieve an approximate pressure close to the desired pressure on the throat or esophagus of the patient 5. This applied pressure is observed by the device 100 and transmitted to a corresponding device 200 with a display screen 215. Second, the physician rotates 129 the pressure dial 110 to set the device 100 to the desired or prescribed pressure. Rotating the pressure dial 110 in one direction increases pressure on the esophagus by causing the threaded central stem 135, sensing component 130 and pressure focusing plate 180 to move longitudinally along a path of travel 139 away from the strap bracket 12 and toward the neck 7 of the patent 5, and from a decreased pressure position 139a to an increased pressure position 139b as shown in FIG. 1D. The semi-flexible strap bracket 12 flexes to increase its curvature with the side posts 137 of the pressure sensing component 130 remaining engaged in the slots 15a of the strap bracket 12. Rotating the pressure dial 110 in an opposite direction decreases pressure on the esophagus by causing the threaded central stem 135, pressure sensing component 130 and pressure focusing plate 180 to move longitudinally along the path of travel 139 toward the strap bracket 12 and away from the neck 7 and into a decreased pressure position 139a as shown in FIG. 1C. The strap bracket 12 flexes to decrease its curvature with the posts 137 of the pressure sensing component 130 remaining engaged in slots 15a of the strap bracket 12.

Monitoring System 200

Figure 7:
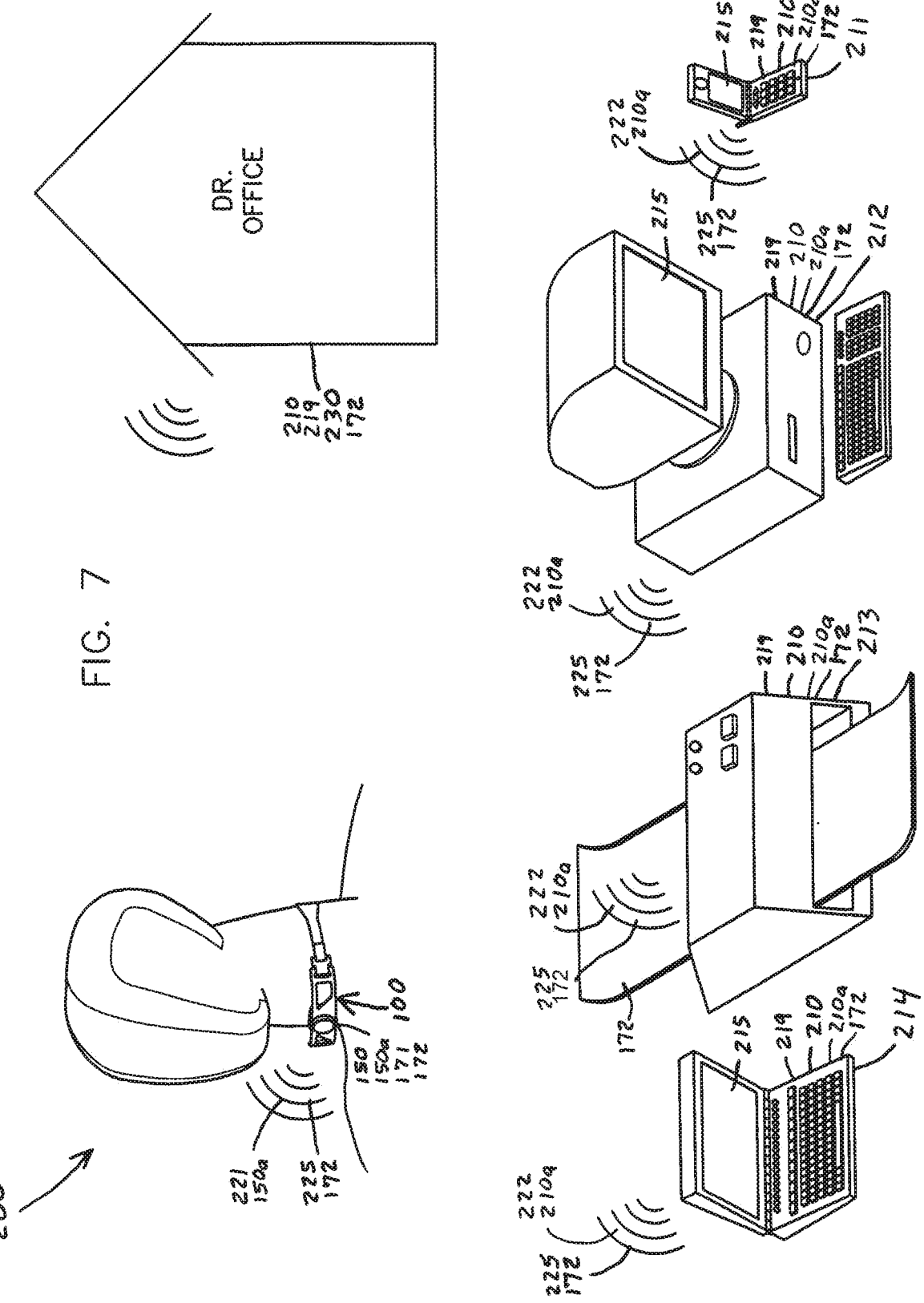
FIG. 7 is a schematic view of the therapeutic pressure applicator and monitoring device and a monitoring system for wireless communication with a cell phone, lap top computer, home computer or printer, and in further communication with a computer in the office of the treating physician via a wired or wireless pathway or the cloud.

The therapeutic pressure applicator and monitoring device 100 and monitoring systems 200 are shown in FIG. 7. The computer module 150 of the monitoring device 100 contains identifying information or ID information 150a that both identifies the specific device and identifies it as a device that wants to send real-time pressure data 172. The CPU 153 of the module 150 is programmed to periodically send signals via its transceiver 153 to a cooperating device 210, such as the cell phone 211 of the patient, a personal home computer 212, printer 213 or laptop computer 214. The office of the treating physician also has a cooperating device 210. Each cooperating devices 210 has an internal programmable microprocessor 219 connected by internal circuitry to a memory, monitor or visual display screen 215, transceiver, user interface or keyboard, and internal or external power source. The cooperating device 210 also includes an audible alarm, and its monitor 215 is capable of displaying information against different colored backgrounds such as a green background 217 or red background 218. Each cooperating device 210 also contains identifying information or ID information 210a that both identifies the specific device and identifies it as a device that wants to receive the real-time pressure data 172. The processor 219 of each cooperating device 200 is programmed or otherwise configured to provide the functionality described herein, and is specifically programmed or configured to receive pressure data 171 and 172 from transceiver 153, compare the cushion pressure data 172 to a desired pressure range criteria, store the data 171 and 172 in its memory, and activate an alarm when the cushion pressure data 171 and 172 is outside the desired pressure range criteria.

The processor 219 of the monitoring device 100 is programmed or otherwise configured to periodically send a request signal 221 containing its ID information 150a looking for the cooperating devices 210. When the cooperating device 210 receives the request signal 221, its processor 219 is programmed or otherwise configured to respond by sending a response signal 222 containing its ID information 210a. When the programmed CPU 151 of the module 150 of the monitoring device 100 receives the response signal 222 and ID information 210a, and the CPU 151 is configured to identify the cooperating device 210 as being a cooperating device 210, the module 150 is programmed or configured to send a data signal 225 via its transceiver 153 with real-time cushion pressure data 172 stored in its memory 152, and store the ID information 210a in its memory 152 with time/date information to log the transmission 225. Similarly, when the CPU 219 of the cooperating device 210 received the data signal 225 and module ID information 150a, and its processor is programmed or otherwise configured to identify the module 150, and then use the real-time cushion pressure data 172 to display the real-time pressure on its monitor 211, and store the ID information 150a and pressure data information 172 in its memory with additional time/date information to log its receipt of the transmission 225. This signal cycle repeats at the periodical time periods for as long as the module 150 and cooperating device 210 remain in communication.

Figure 8B:
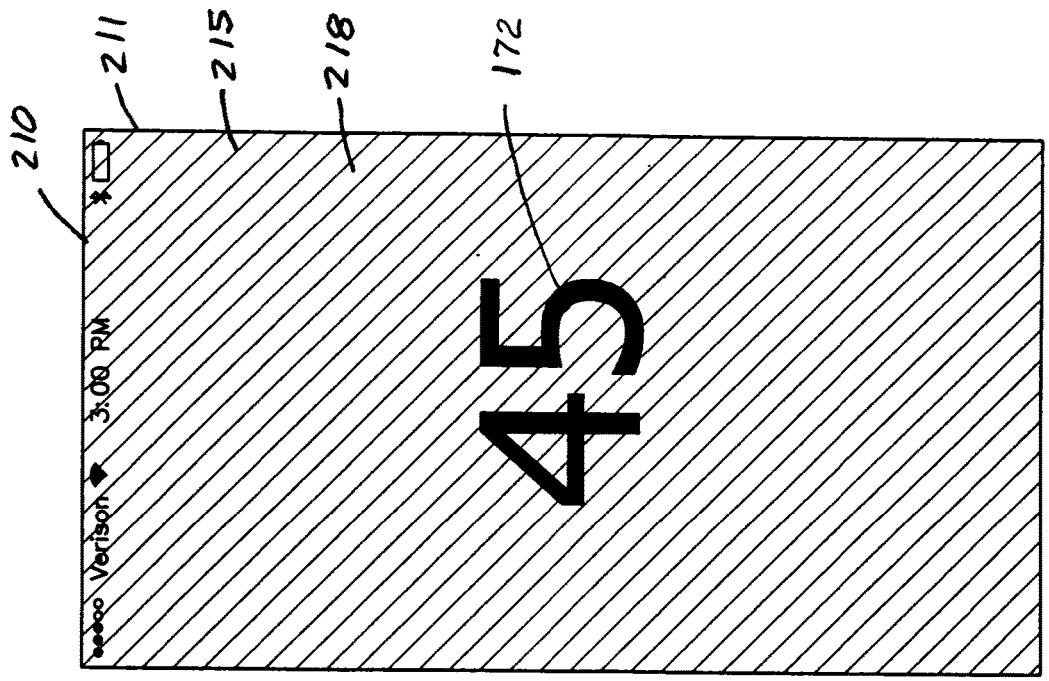
FIG. 8B is a view of a cell phone screen lined for the color red and showing a pressure reading of 45 that is outside of a desired pre-programmed pressure range.
Figure 8A:
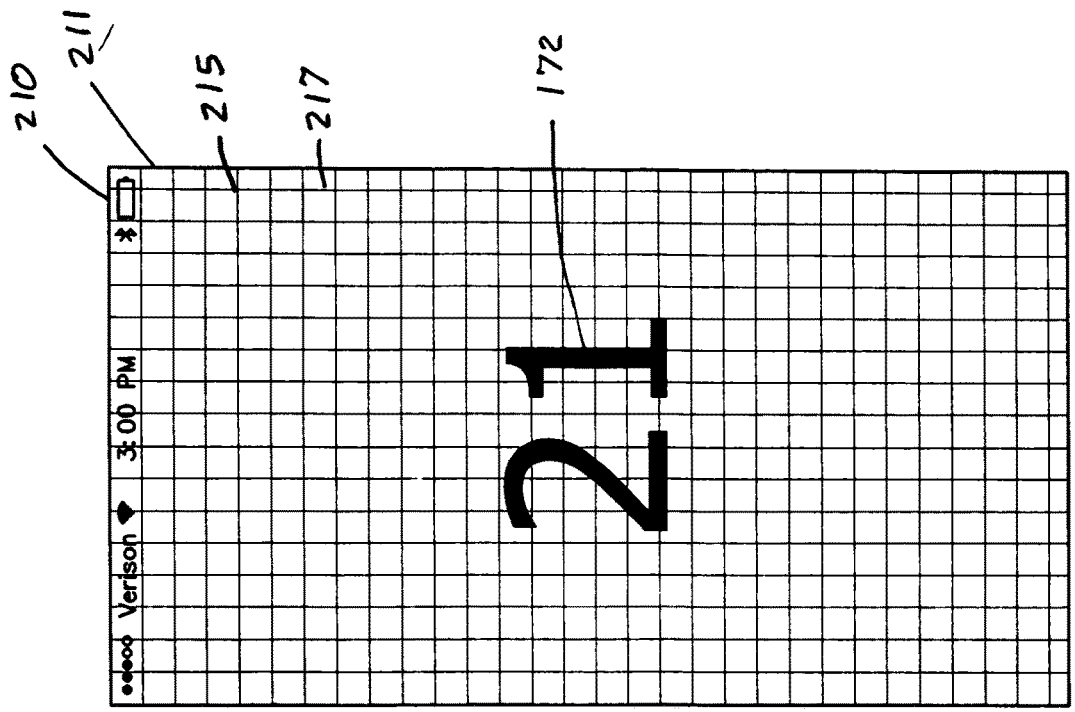
FIG. 8A is a view of a cell phone screen lined for the color green and showing a pressure reading of 21 that is within a desired pre-programmed pressure range.
Figure 9:
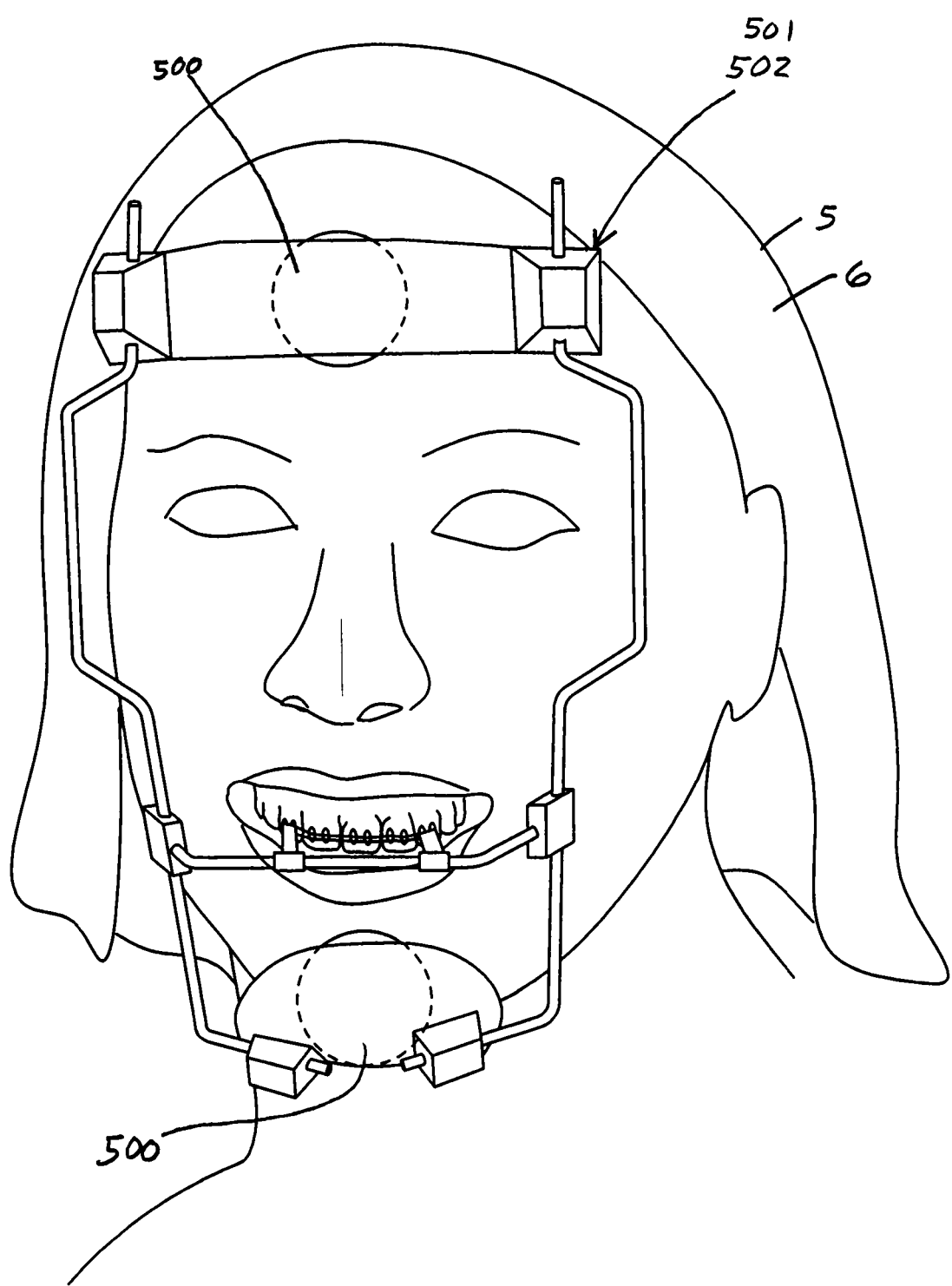
FIG. 9 is an illustrated view of a patient wearing orthodontic headgear with a disc-shaped therapeutic pressure applicator and monitoring device located behind a forehead bracket of the headgear to monitor the pressure applied to the forehead, and a second disc-shaped therapeutic pressure applicator and monitoring device located behind a chin bracket to monitor the pressure applied to the chin.
Figure 10:
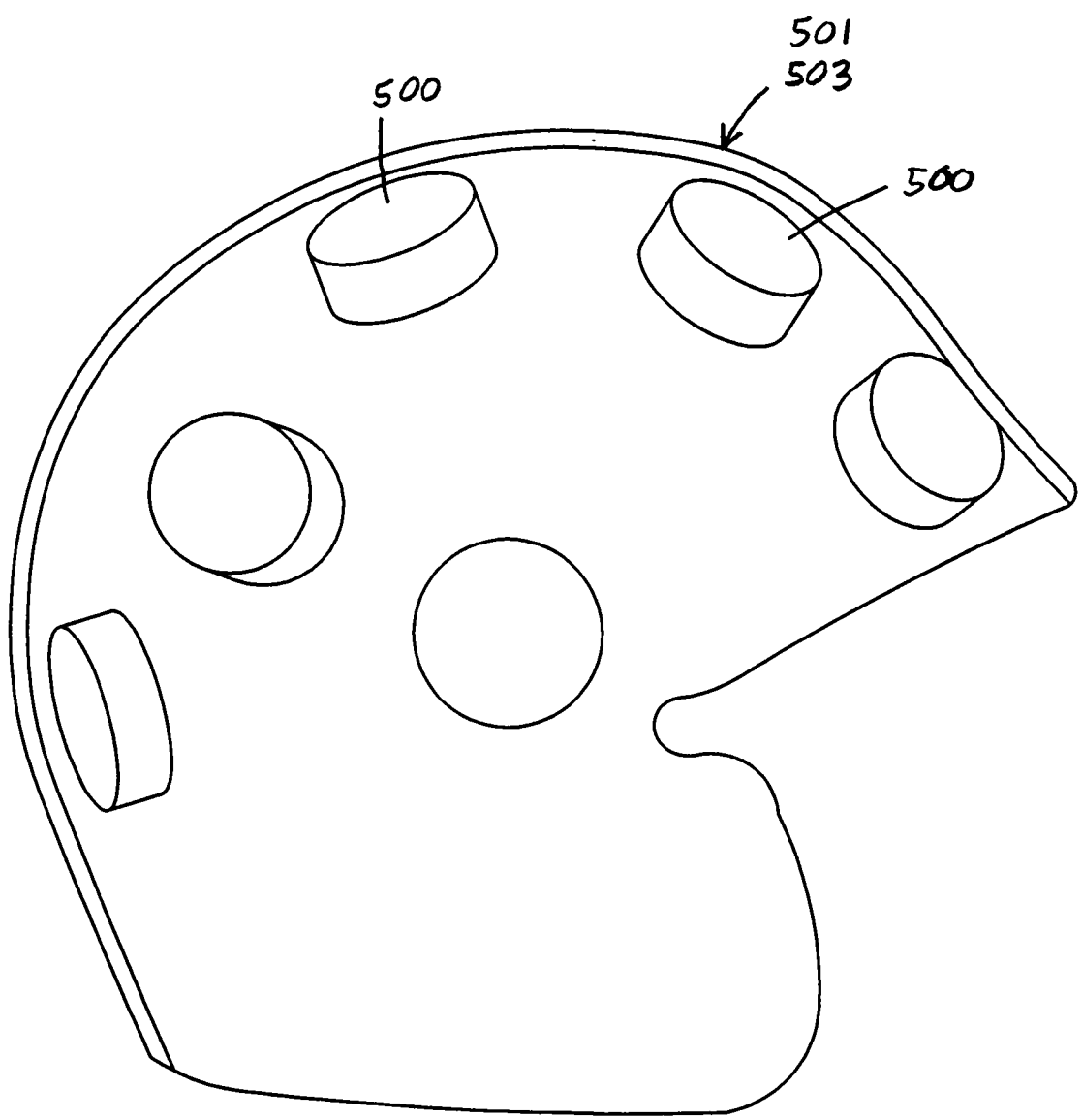
FIG. 10 is a cut away view of a helmet to fit onto the head of a patient with a plurality of disc-shaped therapeutic pressure applicator and monitoring devices located around the interior of the helmet to adjust and monitor the pressure applied to the head.
Figures 11A, 11B:
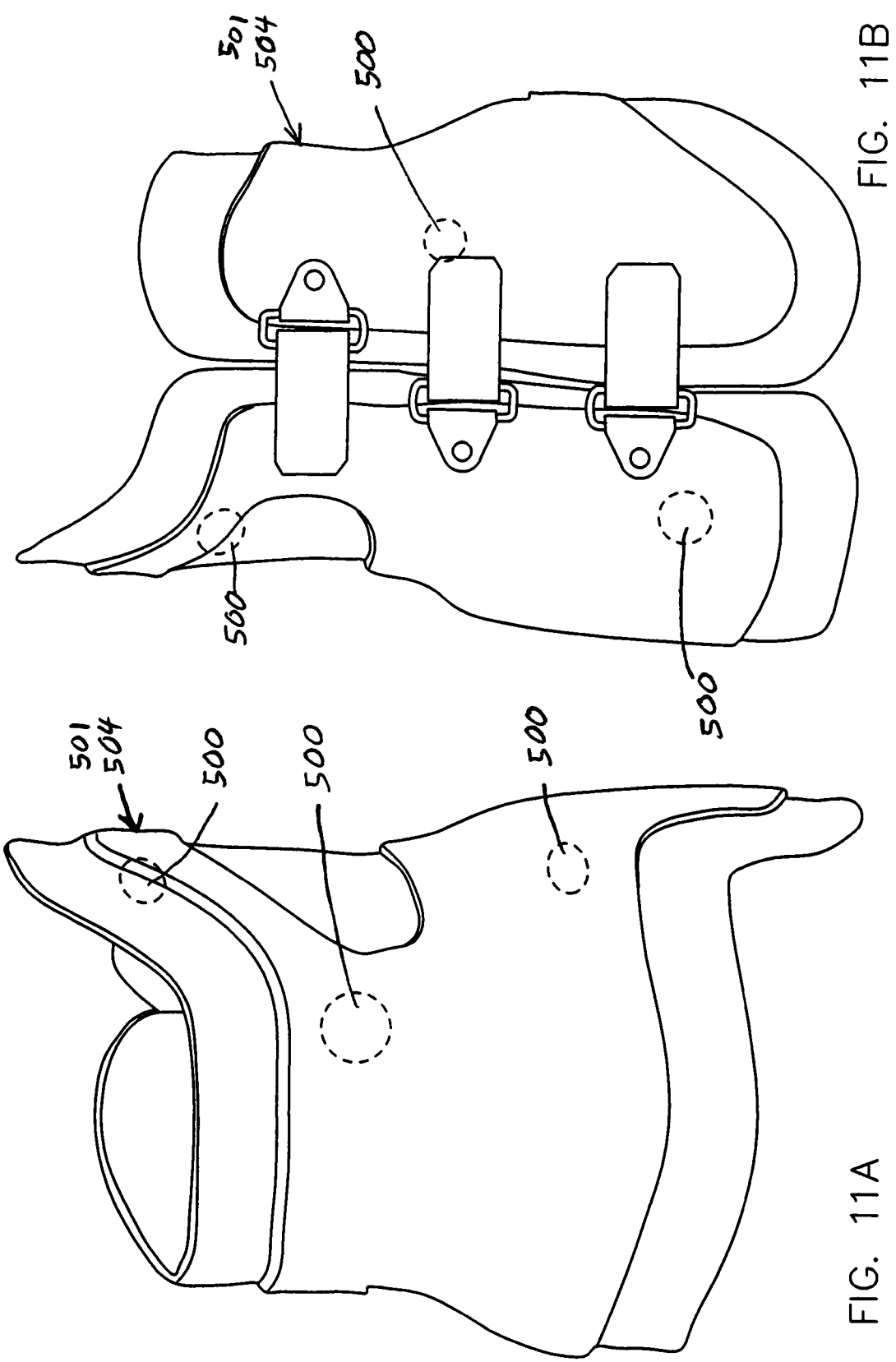
FIG. 11A is a rear perspective view of a back brace to fit around the torso of a patient for spinal realignment treatment with a plurality of disc-shaped therapeutic pressure applicator and monitoring devices located along the back and sides of the brace to adjust and monitor the pressure applied to the back and sides of the patient.
FIG. 11B is a side perspective view of the back brace of FIG. 11B.

The cooperating device 210 is programmed or otherwise configured to display the real-time pressure data 172 on its screen or monitor 215. When the device 210 determines that the real-time pressure data 172 received by the signal 225 is within predetermined range criteria of the prescribed pressure, its programming has the monitor display the real-time pressure data with a green colored background 216 to advise the patient that the real-time pressure is within the prescribed pressure range criteria as shown in FIG. 8A. When the CPU 219 of the device 210 determines that the real-time pressure data 172 is outside the predetermined range criteria for the prescribed pressure, its programming has the monitor 215 display the real-time pressure data 172 against a red 217 background to alert the patient that the real-time pressure is outside the prescribed pressure range criteria as shown in FIG. 8B. The CPU 219 of the device 200 is also programmed or otherwise configures to activate its audible alarm when the real-time pressure data 172 is outside the prescribed pressure range criteria.

The CPU 219 of the cooperating device 210 is also programmed or otherwise configured to send a physician signal 232 to the office 230 of the treating physician. The cooperating device 210 sends the physician signal 232 via a land line, wireless line or the cloud. The programming of the cooperating device 210 sends the physician signal 232 when the real-time pressure data 172 is outside the prescribed pressure range criteria or deviates from a predetermined amount from the prescribed pressure, or at predetermined intervals, such as once a day, week, month, etc. In this way, the treating physician is kept aware that the patient is continuing to use the device 100, the ongoing real-time pressure data 172 observed by the device 100, and when the real-time pressure data is outside a prescribed pressure range criteria. During office visits by the patient to the treating physician, the device 100 can communicate directly with the cooperating device 210 and CPU 219 located at the treating physician office, which has been programmed or otherwise configured to perform the functionality described.

Automated Applicator Embodiment 300

Figure 3A:
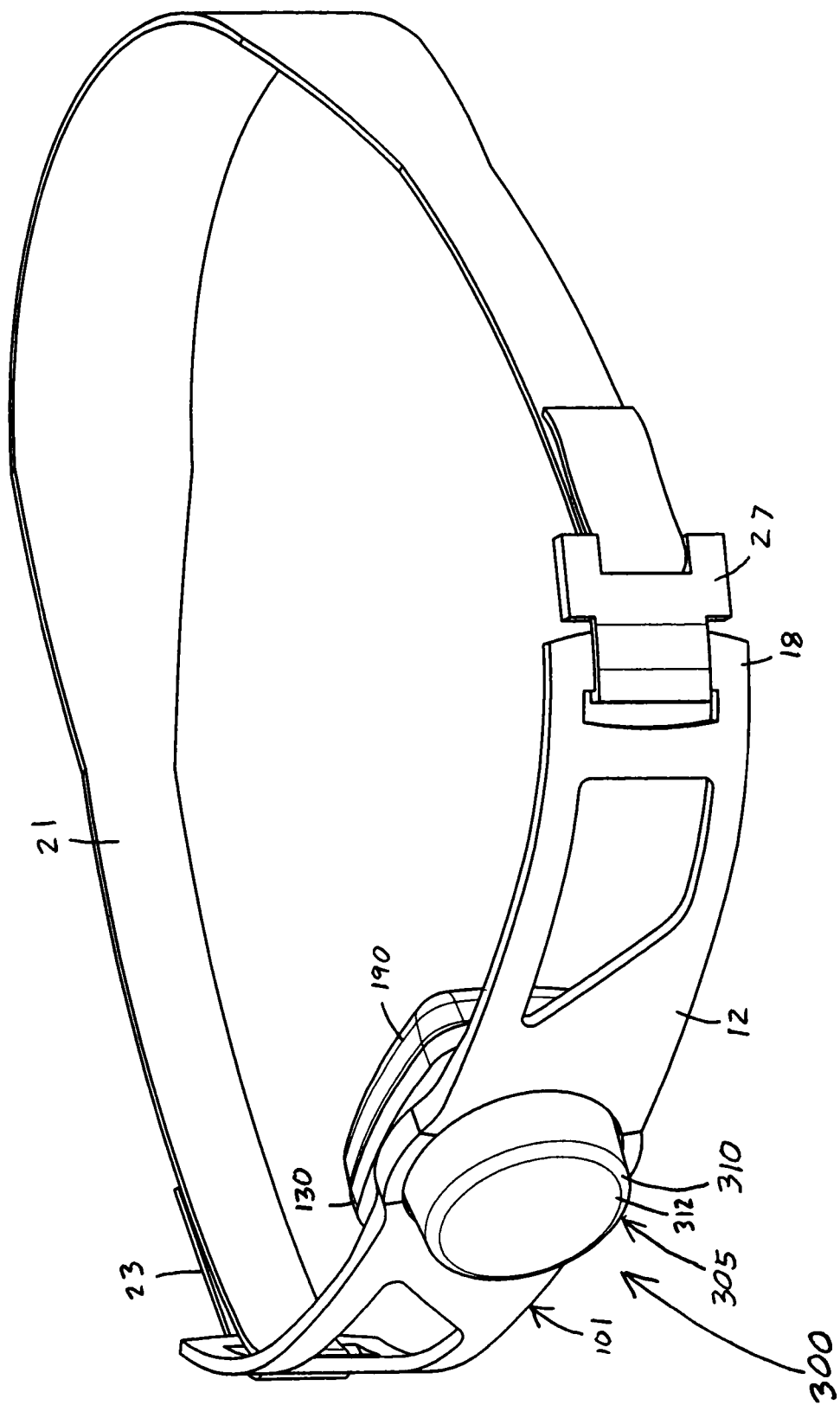
FIG. 3A is a perspective view of a second automated embodiment of the therapeutic pressure applicator and monitoring device used with a conventional neck band to apply pressure to the esophagus of a patient to reduce gastric reflux.
Figure 3B:
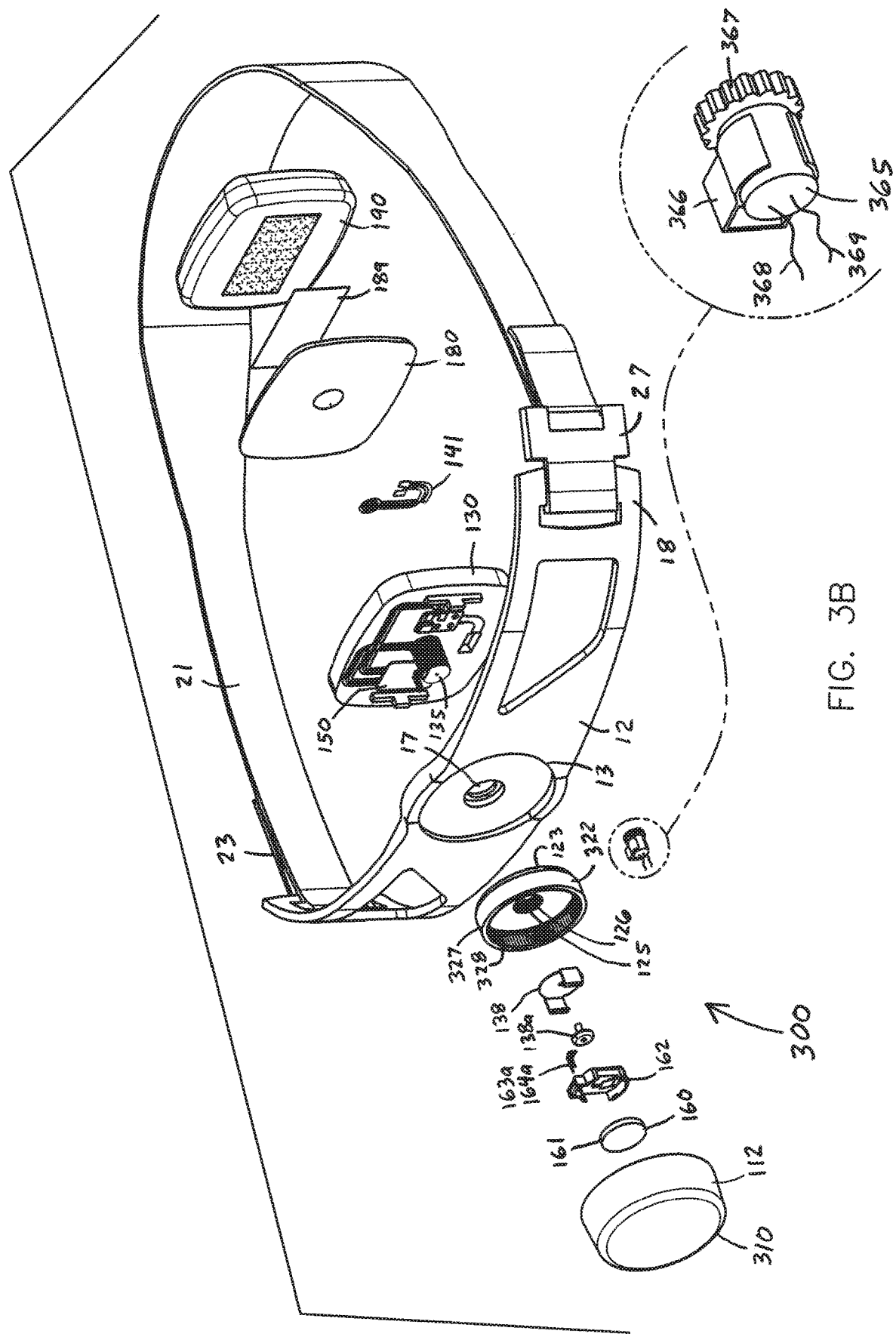
FIG. 3B is an exploded view of the second automated embodiment showing its electrical motor secured to the battery and threaded central post of the sensing component inside the chamber of the pressure dial.

An automated embodiment of the therapeutic pressure applicator and monitoring device 300 is shown in FIGS. 3A and 3B. The automated device 300 automatically adjusts the pressure applied to the neck 5 of the patient 5 so that the applied pressure is at a specific predetermined pressure or within a specific predetermined pressure range. The applicator 300 has a securing mechanism 101 in the form of the conventional neck band 11, and many of the components of the pressure adjusting mechanism 305 of the applicator 300 are interchangeable with the pressure adjusting mechanism 105 of the manually applicator 100. The pressure adjusting mechanism 305 of the automated applicator 300 has the same pressure sensor sensing component 130, sensor 140, computer module 150, power supply 160, pressure focusing plate 180 and cushion 190 as the manual applicator 100. The pressure dial 310 and programming of the CPU 151 of the automated applicator 300 are modified to incorporate a small electric motor 365 to automatically rotate the pressure dial 310 to maintain the applied pressure at the prescribed pressure or within a specific predetermined pressure range of the prescribed pressure.

The pressure adjusting dial 310 of the automated applicator 300 uses a knob 312 the same as knob 112 in applicator 100, but has a modified base 322. The base 322 has the same flat rear surface 123, central opening 125 with a threaded sidewall 126 as in applicator 100, so that the rotation 129 of the dial 310 inwardly or outwardly moves the pressure sensing component 130 and focusing plate 180 along the linear path of travel 139 between increased and decreased pressure positions 139a and 139b. The base 322 has a modified rim 327 with an inside wall 328 having geared teeth around its circumference. The electric motor 365 is fixed at a stationary location inside the chamber 115 of the pressure dial 310. The motor 365 is preferably mounted by a clip 366 to the battery 161 and its casing 162, which are fixed on the non-rotating stem 135 of the pressure sensing component 130. The drive shaft of the motor 365 has a toothed sprocket 367 that drivingly mates and is in rotatable driving engagement with the gear teeth of the base sidewall 328.

The motor 365 is in electrical communication with the power supply 160 via the computer module 150 and its programmed CPU 151. The motor 365 has input and output leads 368 and 369. These leads 368 and 369 are routed through the channel 136a in the stem 135 and along the front surface 132 of the pressure sensing component 130 to motor input and output terminals 158 and 159 of the computer module 150. When the programmed CPU 151 detects that the real-time pressure data 172 is above or below the programmed prescribed pressure or prescribed pressure range, the programmed CPU sends electrical power to activate the motor 365 to rotate its drive sprocket 367 clockwise or counterclockwise depending on whether the real-time pressure data is above or below the prescribed pressure or prescribed pressure range. The rotation of the sprocket 367 drivingly rotates 129 the base 322 and knob 112 of the pressure adjusting dial 310 clockwise or counterclockwise, and moves the pressure sensing component 130 and focusing plate 180 inward or outward along a linear path of travel 139 to a decreased or increased pressure position 139a or 139b until the real-time pressure data equals the prescribed pressure or is within the prescribed pressure range.

Universal Bracket Embodiment 400

Figure 4A:
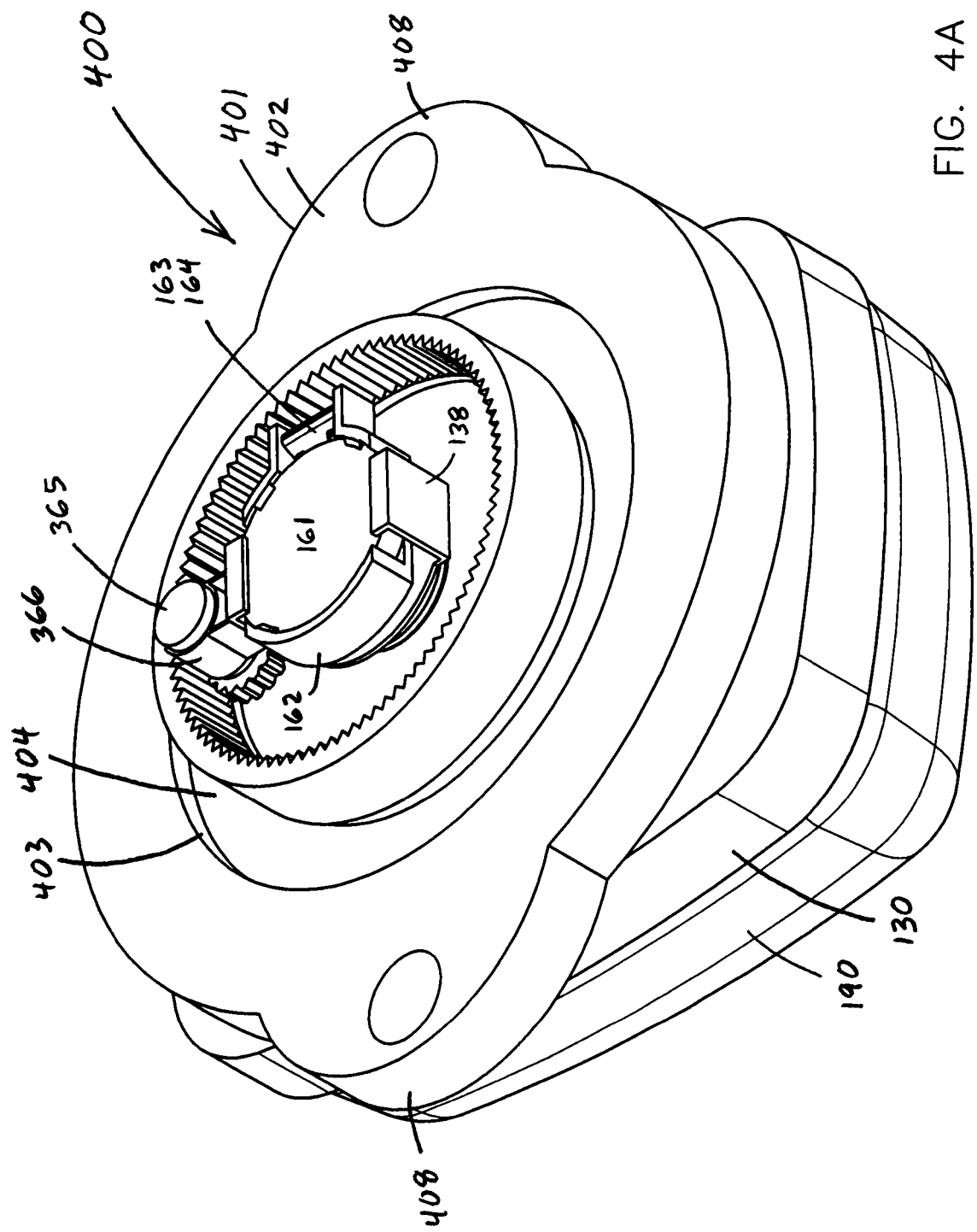
FIG. 4A is a third embodiment of therapeutic pressure applicator and monitoring device used with a universal securement bracket with the dial removed to show the battery and motor.
Figure 4B:
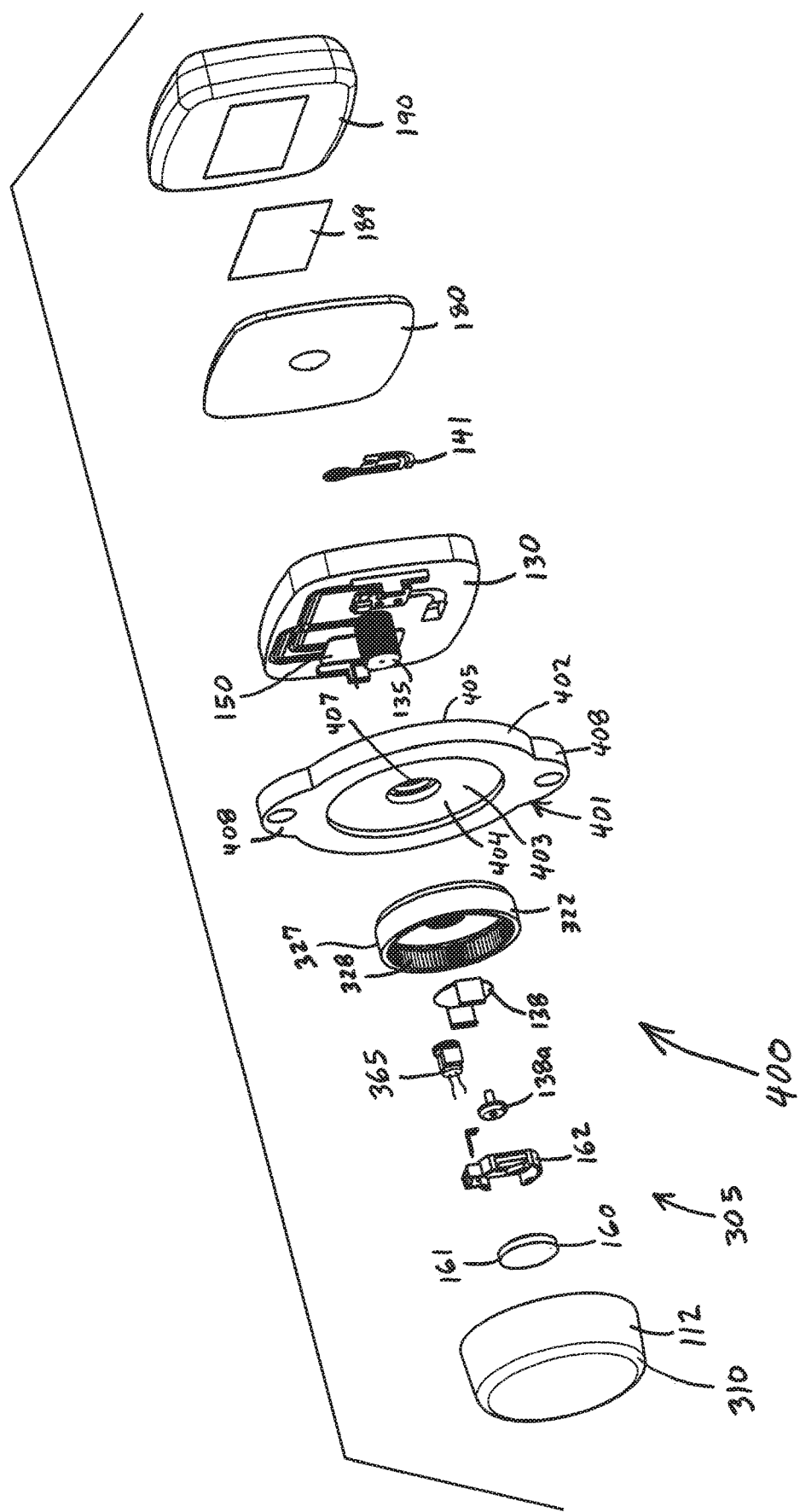
FIG. 4B is an exploded view of the third embodiment with its universal securement bracket.

An embodiment of the therapeutic applicator 400 with a more universal securement mechanism is shown in FIGS. 4A and 4B. The applicator 400 has the same pressure adjusting mechanism 305 as in the automated applicator 300, but the securing mechanism 401 is in the form of a universal securing bracket 402. The bracket 402 has a central recess 403, front and rear surfaces 404 and 405, a central opening 407 and opposed lateral ends 408. The rear surface 405 of the strap bracket 402 has two spaced slots 415a. The common center of the central recess 403 and opening 407 forms a centerline 409 for the applicator 400. A strap (not shown) or some other form of fastener is secured to each of those lateral ends 408 to secure the device 400 to the body of a patient 5.

Disc-Shaped Applicator Embodiment 500

A disc-shaped embodiment of the therapeutic pressure applicator and monitoring device 500 is shown in FIGS. 5A-D. The disc or puck shaped device 500 is used with medical pressure therapy gear 501 worn by the patient 5, such as the orthodontic headgear 502, helmet 503 or back brace 504 shown in FIGS. 9-11. When the pressure applicator and monitoring device 500 is used with orthodontic head gear 502, the securement mechanism 101 is preferably a Velcro® fastener or adhesive 504 that secures the applicator to the forehead and chin bands of the orthodontic headgear. Alternately, when used with a rigid or semi-rigid helmet 503 or back brace 504, the device 500 is sized to snuggly and firmly fit into a cooperating circular opening or recess 506 formed in the helmet or back brace, or a Velcro® fastener (not shown) can also be used to secure the device 500 in the recess 506.

Figure 5D:
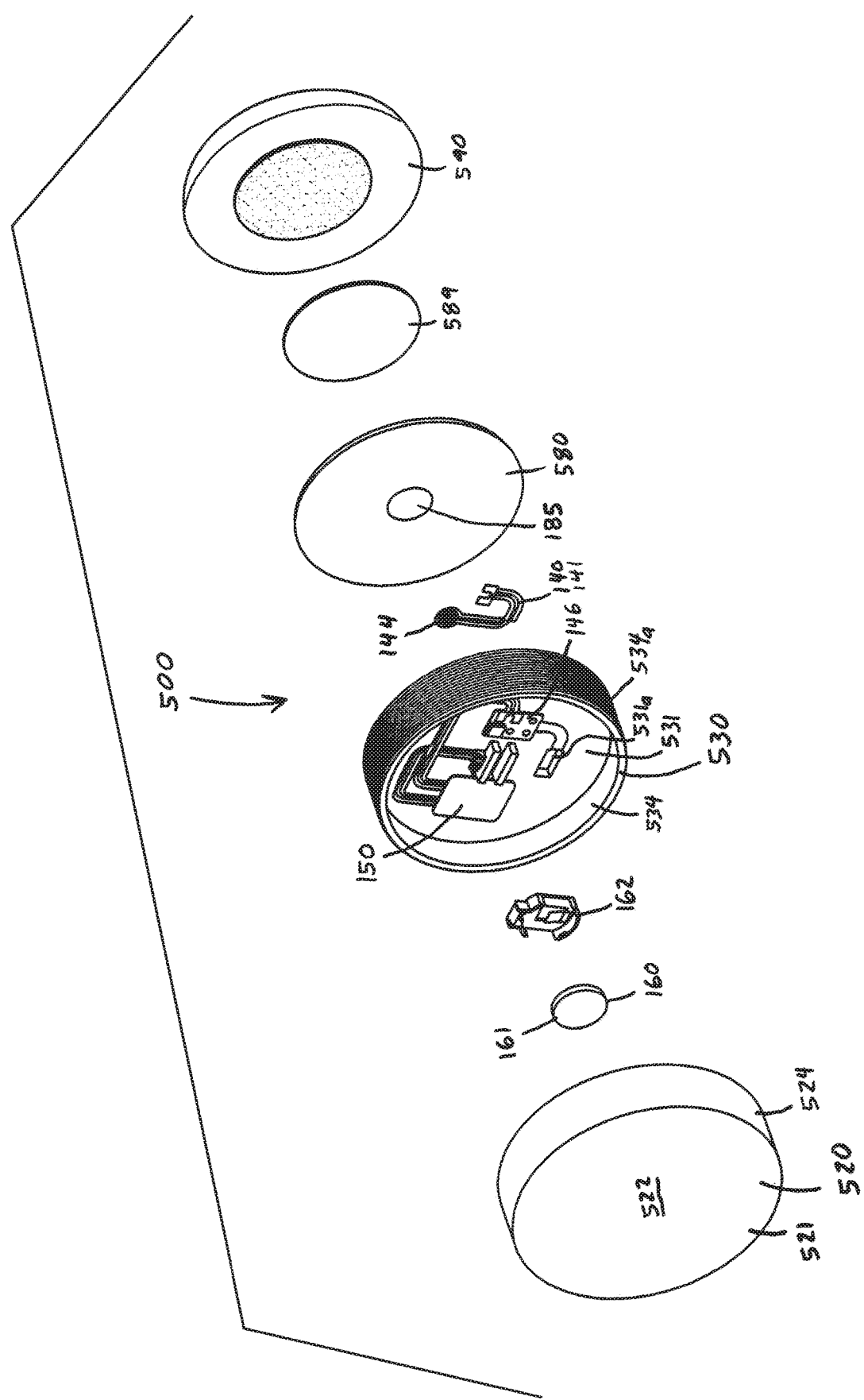
FIG. 5D is an exploded view of the fourth disc-shaped embodiment showing its disc-shaped housing, pressure sensing component with its internal power supply, computer module and pressure gauge, pressure focusing plate with its central button and Velcro® fastener, and cushion.

The pressure adjusting mechanism 510 of the disc-shaped device 500 has a central axis 511 and a rigid, disc-shaped housing 520 as shown in FIG. 5A. The housing has a generally flat circular front plate 521 with front and rear surfaces 522 and 523, and a rearwardly extending tube or sidewall 524 extending around the perimeter of the plate 521 as shown in FIGS. 5B-D. The tube 524 has a threaded inner surface 524a and a uniform diameter along its length. The housing 520 is firmly and non-rotationally secured by the Velcro® strip 505 or otherwise fixed in the cooperating opening 506 to the medical gear 500. The threaded housing tube 524 allows for relative rotational movement 529 of the other components as discussed below.

The pressure sensing component 530 of the disc-shaped device 500 is rigid and preferably made of ABS plastic. The sensing component 530 has a main body 531 with generally flat front and rear surfaces 532 and 533 and a thickness of about 0.5 inches as shown in FIGS. 5B-D. The sensing component 530 and its main body 531 have a generally circular shape with a diameter of about 1.0 inch. A tubular shaped outer structure 534 having a length of about 0.5 inches extends around the perimeter of the main body 131. The outer rim 534 has a threaded outer surface 534a and a uniform diameter along its length so that it flushly engages and threadably mates with threaded inner surface 524a of the housing 520. The outer tube 534 has a forward extending tube portion 535a with a length of about 0.25 inches, and a rearwardly extending rim portion 536 with a length of about 0.25 inches. The forward tube portion 535 forms a chamber 537 that encloses its internal components, and has an end or tip 537a that forms a limit stop to prevent the sensing component from being over-rotated and crushing its internal components. The rearward rim portion 536 has an end with an inwardly facing securement notch 136a that extends around the circumference of the tubular rim 534. The notch 536a has an inwardly sloped or angled cross-sectional shape.

The pressure sensing component 530 has two spaced central posts 537a that extend from its front surface 532. The battery securement clip 538 is secured to the posts by an adhesive or some other form of fastener. The main body 131 has three openings. One opening is sized to matingly receive a computer module. A second opening is sized to matingly receive a base of a force sensor. A third opening 531a is used to route the sensor 141 leads from the front 532 of the main body 531 to the rear 533 of the main body.

The pressure gauge 140, computer module 150 and power supply 160 are the same as in the first embodiment 100. The focusing plate 580, Velcro® strip 589 and cushion 590 are the same as the focusing plate 180, Velcro® strip 189, and cushion 190 of the first embodiment except that they are round to correspond to the round shapes of the housing 510. In this embodiment, the housing 510, sensing component 530, focusing plate 580 and cushion 590 are all disc-shape when viewed from the front and all have a center aligned with the centerline 511 of the device 500.

The pressure sensing component 530 is threadably fixed to the housing 510 to allow rotational movement 529 of the sensing component 530 relative to the housing 510, which results in a linear movement 539 of the sensing component 530, focusing plate 580 and cushion 590. The rotation of the housing 510 in one direction relative to the sensing component 530 causes linear movement 539 of the rear plate 521 of the housing 510 relative to the main body 531 of the sensing component 530, as well as the focusing plate 580 and cushion 590. This movement 539 cause the sensing component 530, focusing plate 580 and cushion 590 to move between a retracted decreased pressure position 539a and an extended increased pressure position 539b, which results in the compression or decompression of the cushion as shown in FIGS. 5B and 5C. As discussed above, the increased compression of the cushion 590 increases the pressure exerted by the cushion on the focusing plate 180 as in FIG. 5C, which increases the force or pressure exerted by the front surface 186 of the focusing plate button 185 on the contact area of the rear surface 143 of the sensor 141. The reduced compression of the cushion 590 reduces the pressure exerted by the cushion on the focusing plate 180 as in FIG. 5B.

While the invention has been described with reference to preferred embodiments, it will be understood by those skilled in the art that various changes may be made and equivalents may be substituted without departing from the broader aspects of the invention.

We claim:

1. A therapeutic pressure applicator and monitoring device for applying pressure to a part of a human body, the therapeutic pressure applicator and monitoring device comprising:
    a securement member adapted to secure to the part of the human body, said securement member having a securement bracket with a rear side facing toward the part of the human body, a front side facing away from the part of the human body and a bracket opening between said front and rear sides;
    a pressure adjusting mechanism having a pressure dial positioned on said front side of said securement member and a pressure sensing component positioned on said rear side of said securement member, said sensing component having a main body with front and rear main body surfaces, a mounting rim extending rearwardly from said rear main body surface and a threaded post extending forward from said front main body surface and through said bracket opening, said pressure dial having an interior threaded opening in threaded engagement with said threaded post, said pressure dial being selectively rotatable about said post to move said sensing component along a path of travel between retracted and extended positions relative to said securement bracket;
    a computer module and power source held by and enclosed in said pressure adjusting mechanism, said module having a processor, memory and transceiver connected by an internal circuitry, and said processor and transceiver being in electrical powered communication with said power source;
    a force sensor positioned along said rear main body surface of said sensing component and being in electrical sensing communication with said processor;
    a pressure focusing plate having front and rear sides, said plate rear side having a predetermined rear surface area, said focusing plate being held by said mounting rim of said sensing component with said front side positioned in registry over said rear main body surface; said front side having a pressure focusing structure forming a contact zone, said contact zone being smaller than said predetermined rear surface area, and said contact zone being aligned over and in force transmitting engagement with said sensor; and,
    a cushion having front and rear cushion surfaces, said front cushion surface being secured to said rear side of said focusing plate, and said rear cushion surface being adapted to apply the applied pressure to the part of the human body.

2. The therapeutic pressure applicator and monitoring device of claim 1, and wherein said pressure focusing structure is a central button with a curved surface.

3. The therapeutic pressure applicator and monitoring device of claim 2, and wherein said sensing component has a main body perimeter and said focusing plate has a focusing plate perimeter, and said mounting rim extends from said main body perimeter and circumferentially engages said focusing plate perimeter.

4. The therapeutic pressure applicator and monitoring device of claim 3, and wherein said mounting rim has an inwardly facing radial notch, and said focusing plate perimeter is held by said radial notch.

5. The therapeutic pressure applicator and monitoring device of claim 4, and wherein said contact zone has a predetermined area, and said radial notch is sized and spaced from said main body front surface to provide a radial gap between said radial notch and said focusing plate perimeter, said radial gap allowing said focusing plate to pivot about said curved surface of said button while maintaining said predetermined area of said contact zone.

6. The therapeutic pressure applicator and monitoring device of claim 5, and wherein said sensor is a force-sensing sensor that changes its resistance when a force is applied to a surface of said sensor.

7. The therapeutic pressure applicator and monitoring device of claim 6, and wherein said main body rear surface has a recess with a recess surface, and said sensor is positioned in said recess against said rear recess surface.

8. The therapeutic pressure applicator and monitoring device of claim 2, and wherein said threaded post, force sensor and button are in substantially linear alignment.

9. The therapeutic pressure applicator and monitoring device of claim 8, and wherein said opening in said securement bracket is centrally located and forms a central axis for said pressure adjusting mechanism, and wherein said dial, sensor, button and cushion each have a center located on said central axis.

10. The therapeutic pressure applicator and monitoring device of claim 1, and wherein said power source is a battery and said dial has an internal compartment, said threaded post has a top surface, said battery is held by said top surface in said internal compartment, said computer module is held by said main body of said sensor component, said force sensor is secured to a pressure gauge, and said pressure gauge is held by said main body of said sensing component.

11. The therapeutic pressure applicator and monitoring device of claim 1, and wherein the therapeutic pressure applicator and monitoring device is used in a monitoring system, and wherein said focusing plate focuses the applied pressure into a focused load applied by said contact zone onto said sensor, and said sensor communicates real-time focused pressure data to said processor, and said processor converts said focused pressure data to real-time cushion pressure data and stores said real-time cushion pressure data in said memory of said computer module.

12. The therapeutic pressure applicator and monitoring device of claim 11, and wherein said monitoring system further comprises a second device with a processor, memory, transceiver and display screen, and wherein said processor of said therapeutic pressure applicator and monitoring device transmits said real-time cushion pressure data to said processor of said second device, and said processor of said second device displays said real-time cushion pressure data on said display screen and stores said real-time cushion pressure data in said memory of said second device.

13. The therapeutic pressure applicator and monitoring device of claim 11, and wherein said pressure dial has an internal chamber and an interior surface with geared teeth, and said chamber contains a motor with a drive sprocket in rotatable driving engagement with said geared teeth, said processor contains predetermined desired pressure range data, said motor is in electric communication with said processor, and said processor is programmed to activate said motor and rotate said dial when said real-time cushion pressure data is outside said predetermined pressure range.

14. A therapeutic pressure applicator and monitoring device to apply an applied pressure to a body part of a person wearing treatment gear for long-term pressure treatment of the body part, the treatment gear having an inside surface adapted to engage the body part, and the inside surface having at least one securement recess, the therapeutic pressure applicator and monitoring device comprising:
  a pressure adjusting mechanism having a housing and a sensing component, said housing having a base and a threaded rearward tube, said base having front and rear surfaces, said sensing component having a main body, a threaded outer tube forming a forward tube and a rearward radial mounting rim, said main body having front and rear main body surfaces, said rearward and forward tubes being in mated threaded engagement, said housing and sensing component forming an interior chamber, and said sensing component being rotatable relative to said housing to move said sensing component along a path of travel between retracted and extended positions relative to said base of said housing;
  a computer module and power source held by said pressure adjusting mechanism in said interior chamber, said module having a processor, memory and transceiver connected by an internal circuitry, and said processor and transceiver being in electrical powered communication with said power source;
  a force sensor positioned along said rear main body surface of said sensing component and being in electrical sensing communication with said processor; a pressure focusing plate having front and rear sides, said plate rear side having a predetermined rear surface area, said focusing plate being held by said radial mounting rim of said sensing component with said front side positioned in registry over said rear main body surface; said front side having a pressure focusing structure forming a contact zone, said contact zone being smaller than said predetermined rear surface area, and said contact zone being aligned over and in force transmitting engagement with said sensor; and,
  a cushion having front and rear cushion surfaces, said front cushion surface being secured to said rear side of said focusing plate, and said rear cushion surface being adapted to apply the applied pressure to the body part of the person.

15. The therapeutic pressure applicator and monitoring device of claim 14, and wherein said pressure focusing structure is a central button with a curved surface.

16. The therapeutic pressure applicator and monitoring device of claim 15, and wherein said sensing component has a main body perimeter and said focusing plate has a focusing plate perimeter, and said mounting rim extends from said main body perimeter and circumferentially engages said focusing plate perimeter.

17. The therapeutic pressure applicator and monitoring device of claim 16, and wherein said mounting rim has an inwardly facing radial notch, and said focusing plate perimeter is held by said radial notch.

18. The therapeutic pressure applicator and monitoring device of claim 17, and wherein said contact zone has a predetermined area, and said radial notch is sized and spaced from said main body front surface to provide a radial gap between said radial notch and said focusing plate perimeter, said radial gap allowing said focusing plate to pivot about said curved surface of said button while maintaining said predetermined area of said contact zone.

19. The therapeutic pressure applicator and monitoring device of claim 18, and wherein said sensor is a force-sensing sensor that changes its resistance when a force is applied to a surface of said sensor.

20. The therapeutic pressure applicator and monitoring device of claim 14, and wherein said base of said housing, main body of said sensing component, focusing plate and cushion each have a circular perimeter, and wherein a rearward tubular column extends rearwardly from said perimeter of said base, a forward extending tubular column extends forwardly from said perimeter of said main body, and said housing, sensing component, focusing plate and cushion combine to form a disc-shaped structure.

21. The therapeutic pressure applicator and monitoring device of claim 14, and wherein said rearward threaded surface of said housing is an inside surface of a rearward tubular column, and said forward threaded surface of said sensing component is an outside surface of a forward tubular column.

22. The therapeutic pressure applicator and monitoring device of claim 14, and wherein the therapeutic pressure applicator and monitoring device is used in a monitoring system, and wherein said focusing plate focuses the applied pressure into a focused load applied by said contact zone onto said sensor, and said sensor communicates real-time focused pressure data to said processor, and said processor converts said focused pressure data to real-time cushion pressure data and stores said real-time cushion pressure data in said memory of said computer module.

23. The therapeutic pressure applicator and monitoring device of claim 14, and wherein said monitoring system further comprises a second device with a processor, memory, transceiver and display screen, and wherein said processor of said therapeutic pressure applicator and monitoring device transmits said real-time cushion pressure data to said processor of said second device, and said processor of said second device displays said real-time cushion pressure data on said display screen and stores said real-time cushion pressure data in said memory of said second device.

24. The therapeutic pressure applicator and monitoring device of claim 14, and wherein said pressure dial has an internal chamber and an interior surface with geared teeth, and said chamber contains a motor with a drive sprocket in rotatable driving engagement with said geared teeth, said processor contains predetermined desired pressure range data, said motor is in electric communication with said processor, and said processor is programmed to activate said motor and rotate said dial when said real-time cushion pressure data is outside said predetermined pressure range.

25. Pressure treatment gear for applying and monitoring applied pressure to a body part of a person, the pressure treatment gear comprising:
  gear worn by the person on the body part for long-term pressure treatment of the body part, said gear having an inside surface adapted to engage the body part, and said inside surface having at least one securement recess;
  a pressure adjusting mechanism having a housing and a sensing component, said housing having a base and a threaded rearward tube, said base having front and rear surfaces, said sensing component having a main body, a threaded outer tube forming a forward tube and a rearward radial mounting rim, said main body having front and rear main body surfaces, said rearward and forward tubes being in mated threaded engagement, said housing and sensing component forming an interior chamber, and said sensing component being rotatable relative to said housing to move said sensing component along a path of travel between retracted and extended positions relative to said base of said housing;

a computer module and power source held by said pressure adjusting mechanism in said interior chamber, said module having a processor, memory and transceiver connected by an internal circuitry, and said processor and transceiver being in electrical powered communication with said power source;

a force-sensing sensor positioned along said rear main body surface of said sensing component and being in electrical sensing communication with said processor;

a pressure focusing plate having front and rear sides and a perimeter, said plate rear side having a predetermined rear surface area, said focusing plate being held by said mounting rim of said sensing component with said front side positioned in registry over said rear main body surface; said front side having a pressure focusing structure forming a contact zone, said contact zone being smaller than said predetermined rear surface area, and said contact zone being aligned over and in force transmitting engagement with said sensor; and, a cushion having front and rear cushion surfaces, said front cushion surface being secured to said rear side of said focusing plate, and said rear cushion surface being adapted to apply the applied pressure to the body part of the person.

* * * * *

UNITED STATES PATENT AND TRADEMARK OFFICE
CERTIFICATE OF CORRECTION

PATENT NO. : 11,141,105 B2
APPLICATION NO. : 15/457856
DATED : October 12, 2021
INVENTOR(S) : Daniel Paul Armbrust et al.

Page 1 of 1

It is certified that error appears in the above-identified patent and that said Letters Patent is hereby corrected as shown below:

In the Specification

Column 5, Lines 66-67, "conventional band REZA BAND® device" should be --conventional REZA BAND® device--.

Signed and Sealed this
First Day of March, 2022

Drew Hirshfeld
*Performing the Functions and Duties of the
Under Secretary of Commerce for Intellectual Property and
Director of the United States Patent and Trademark Office*